US012369955B2

(12) United States Patent
Mast et al.

(10) Patent No.: US 12,369,955 B2
(45) Date of Patent: Jul. 29, 2025

(54) RATCHETING RAPID ROD REDUCTION INSTRUMENT

(71) Applicant: ZIMMER BIOMET SPINE, INC., Westminster, CO (US)

(72) Inventors: Randall G. Mast, Denver, CO (US); Allison Christine Capote, Boulder, CO (US); Caleb Lee Stoll, Broomfield, CO (US)

(73) Assignee: Highridge Medical, LLC, Westminster, CO (US)

( * ) Notice: Subject to any disclaimer, the term of this patent is extended or adjusted under 35 U.S.C. 154(b) by 309 days.

(21) Appl. No.: 17/737,715

(22) Filed: May 5, 2022

(65) Prior Publication Data

US 2022/0354548 A1 Nov. 10, 2022

Related U.S. Application Data

(60) Provisional application No. 63/185,858, filed on May 7, 2021.

(51) Int. Cl.
*A61B 17/88* (2006.01)
*A61B 17/70* (2006.01)

(52) U.S. Cl.
CPC ...... *A61B 17/7086* (2013.01); *A61B 17/7091* (2013.01)

(58) Field of Classification Search
CPC ............... A61B 17/7086; A61B 17/7091
(Continued)

(56) References Cited

U.S. PATENT DOCUMENTS 10,085,778 B2   10/2018  Semingson et al.
10,136,927 B1   11/2018  Lish et al.
(Continued)

FOREIGN PATENT DOCUMENTS

CN   101365394   2/2009
CN   101972179   2/2011
(Continued)

OTHER PUBLICATIONS

Intention to Grant for United Kingdom Patent Application No. GB2206989.2, dated Jan. 23, 2024 2 pages.
(Continued)

*Primary Examiner* — Eduardo C Robert
*Assistant Examiner* — David C Comstock
(74) *Attorney, Agent, or Firm* — Sheridan Ross P.C.

(57) ABSTRACT

A rod reduction instrument includes an inner sleeve, a first housing portion, a second housing portion, a plurality of engagement members, and a ratchet mechanism. The inner sleeve can include a threaded proximal portion and a distal end. The first housing portion can be positioned over at least a portion of the inner sleeve. The second housing portion can be positioned proximate to the distal end of the inner sleeve. The plurality of engagement members can be adapted to receive a pedicle screw, and are positionable within the second housing portion. The ratchet mechanism can include an engagement feature to selectively engage the threaded proximal portion of the inner sleeve, and a locking mechanism to selectively lock the engagement feature of the ratchet mechanism against the threaded proximal portion of the inner sleeve.

20 Claims, 21 Drawing Sheets

(58) Field of Classification Search
USPC .................................................. 606/86 A, 99
See application file for complete search history.

(56) References Cited

U.S. PATENT DOCUMENTS

| | | | |
|---|---|---|---|
| 10,716,602 B2 | 7/2020 | Fischer | |
| 10,898,241 B2* | 1/2021 | Lish | A61B 17/7083 |
| 10,918,424 B2* | 2/2021 | Stoll | A61B 17/7086 |
| 2007/0213714 A1 | 9/2007 | Justis | |
| 2008/0243190 A1 | 10/2008 | Dziedzic et al. | |
| 2009/0228053 A1 | 9/2009 | Kolb et al. | |
| 2012/0191144 A1 | 7/2012 | Peultier et al. | |
| 2012/0283786 A1 | 11/2012 | Rezach et al. | |
| 2014/0148865 A1* | 5/2014 | Hennard | A61B 17/7086 606/86 A |
| 2014/0315475 A1 | 10/2014 | Parikh et al. | |
| 2015/0051648 A1 | 2/2015 | May et al. | |
| 2015/0066042 A1 | 3/2015 | Cummins et al. | |
| 2015/0100098 A1 | 4/2015 | Moore | |
| 2015/0142067 A1 | 5/2015 | Bess et al. | |
| 2016/0030093 A1 | 2/2016 | Walker | |
| 2016/0106480 A1 | 4/2016 | Zhou et al. | |
| 2017/0252074 A1 | 9/2017 | Semingson et al. | |
| 2021/0161568 A1 | 6/2021 | Stoll et al. | |
| 2023/0346435 A1 | 11/2023 | Stoll et al. | |

FOREIGN PATENT DOCUMENTS

| | | |
|---|---|---|
| CN | 102256558 | 11/2011 |
| CN | 110251221 | 9/2019 |
| GB | 741774 | 12/1955 |
| JP | 2011514830 | 5/2011 |
| JP | 2019177138 | 10/2019 |

OTHER PUBLICATIONS

Official Action for Great Britain Patent Application No. GB2206989.2, dated Aug. 30, 2023 4 pages.
Search Report for Chinese Patent Application No. 201910184040.9, dated Oct. 9, 2021, 2 pages.
Official Action (with English Translation) for Chinese Patent Application No. 201910184040.9, dated Oct. 26, 2021, 14 pages.
Notice of Allowance with English Translation for China Patent Application No. 201910184040.9, dated Mar. 21, 2022, 8 pages.
"European Application Serial No. 19162309.9, Extended European Search Report mailed Jul. 19, 2019", 9 pages.
Search Report (with English translation) for Japanese Patent Application No. 2019-043572, dated Apr. 17, 2020 29 pages.
Notice of Reasons for Refusal (with English translation) for Japanese Patent Application No. 2019-043572, dated May 12, 2020 6 pages.
"Japanese Application Serial No. 2019-043572, Notification of Reasons for Rejection mailed Dec. 22, 2020" (with English Translation), 8 pages.
Decision of Refusal (with English translation) for Japanese Patent Application No. 2019-043572, dated Jul. 27, 2021 7 pages.
Notice of Allowance (with English Translation) for Japan Patent Application No. 2019-043572, dated Feb. 1, 2022 5 pages.
"U.S. Appl. No. 16/295,183, Corrected Notice of Allowability mailed Nov. 23, 2020", 2 pages.
"U.S. Appl. No. 16/295,183, Final Office Action mailed Aug. 5, 2020", 14 pages.
"U.S. Appl. No. 16/295,183, Non Final Office Action mailed Apr. 22, 2020", 13 pages.
"U.S. Appl. No. 16/295,183, Notice of Allowance mailed Oct. 15, 2020", 7 pages.
Official Action for U.S. Appl. No. 17/149,478, dated Aug. 22, 2022, 22 pages.
Search and Examination Report for Great Britain Patent Application No. GB2206989.2, dated Oct. 11, 2022 5 pages.

\* cited by examiner

RATCHETING RAPID ROD REDUCTION INSTRUMENT

CROSS-REFERENCE TO RELATED APPLICATION

This U.S. Non-Provisional Patent application claims the benefit of priority under 35 U.S.C. § 119(e) of U.S. Provisional Patent Application Ser. No. 63/185,858, filed May 7, 2021, the entire disclosure of each of which is hereby incorporated by reference.

TECHNICAL FIELD

The present application generally relates to spinal fusion procedures involving use of rod reduction instruments to assist in securing connecting rods in pedicle screw implants to immobilize one or more vertebrae and, in particular, to a ratcheting rapid rod reduction instrument.

BACKGROUND

A common surgical procedure to correct deformities in the spine involves stabilizing affected vertebral bodies with interbody implants, pedicle screws and connecting rods. The interbody implants are used to replace disc material between the affected vertebral bodies and promote boney fusion between the vertebrae. The pedicle screws and connecting rods are used to stabilize the affected portion of the spine to allow fusion to occur. The portion of the procedure involving rod reduction instruments involves implanting pedicle screws bilaterally in affected vertebral bodies and then connecting the pedicle screw implants with stiff, usually metal, connecting rods to secure the vertebrae in a desired orientation. Often a surgeon is attempting to restore some sort of natural curvature or realign a displaced vertebra (spondylosis). It is not uncommon during these procedures for a surgeon to utilize an instrument designed to assist in leveraging a connecting rod into a pedicle screw to restore alignment, these instruments are commonly referred to as rod reduction instruments. Rod reduction may be necessary due to curvature correction or the degree of misalignment (e.g., to pull a vertebra back into alignment).

SUMMARY

Aspects of the present disclosure are directed to a rod reduction instrument for surgical procedures. In particular, the rod reduction instrument may include an inner portion and an outer portion that are configured to engage one another, while also configured to move relative to or independently of one another. For example, the outer portion may include a top sleeve that rotates relative to a bottom sleeve, and the inner portion may include an inner sleeve that is actuated with the rotation of the top sleeve relative to the bottom sleeve. By way of another example, the outer portion may include an upper housing and a lower housing coupled together and the inner portion may include an inner sleeve configured to actuate relative to the upper housing and lower housing, with support members configured to also actuate relative to at least the lower housing. The rod reduction instrument may include engagement features that are configured to engage a pedicle screw.

The rod reduction instrument may include two different reduction modes of operation, or a dual mode of operation, which allow for rapid or quick operation of the rod reduction instrument or incremental operation of the rod reduction instrument. For example, the rod reduction instrument includes a ratcheting feature or ratchet mechanism which allows for a rapid or quick operation of the rod reduction instrument when engaging with or disengaging from the pedicle screw. By way of another example, the rod reduction instrument includes a fine-tuning feature or fixed mode (e.g., complementary threading, protrusions, detents with captured ball bearings, or the like) which allows for incremental changes when engaging with or disengaging from a pedicle screw. It is noted the ratcheting feature may include a button or switch that allows for a bypassing or disengaging of the fine-tuning feature. In addition, it is noted the fine-tuning feature may be manually actuated or adjusted with a tool such as a T-handle; a hex wrench, a screwdriver, or other tool with a common or proprietary bit; or the like.

Utilizing the rapid or quick operation of the rod reduction instrument may allow for initial positioning against or removal from the pedicle screw. Utilizing the fixed mode may allow for fine-tuning the positioning of the rod reduction instrument against the pedicle screw. In addition, utilizing the fixed mode may allow for the application of an additional force (e.g., such as increased torque), where the rod reduction instrument is binding and/or where an external or internal force is operating on the rod reduction instrument, allowing for a user to manually disengage the rod reduction instrument from the pedicle screw without need for extraordinary measures such as cutting the rod reduction instrument to remove the pedicle screw. Thus, the rod reduction instrument may leverage the mechanical advantage of the threads to overcome external forces jamming the rod reduction instrument.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood the drawings are not necessarily drawn to scale. In certain instances, details that are not necessary for an understanding of the disclosure or that render other details difficult to perceive may have been omitted. In addition, it should be understood that the disclosure is not necessarily limited to the particular embodiments illustrated herein. Further, it should be understood like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
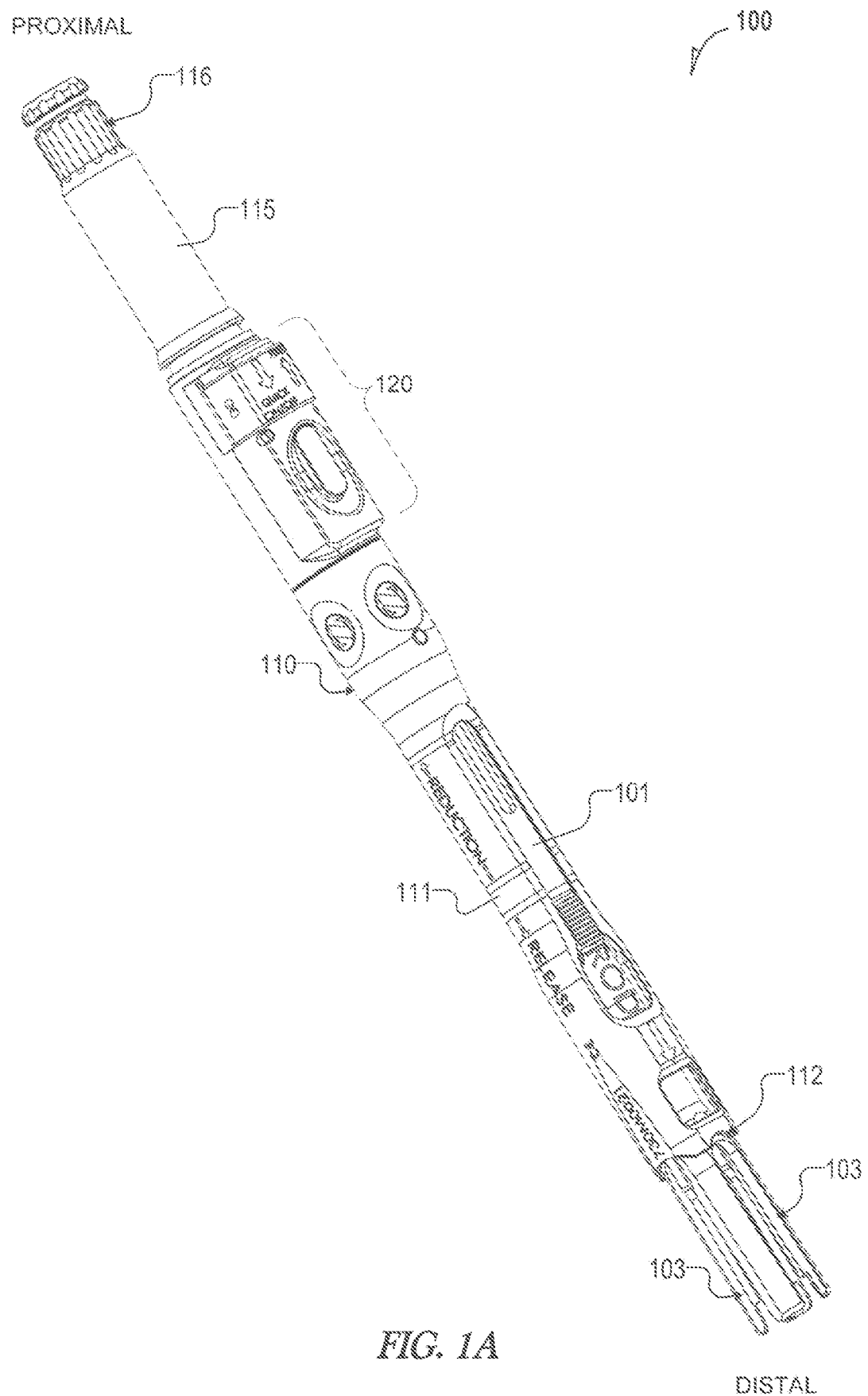
FIG. 1A is an isometric view of a rod reduction instrument, in accordance with example embodiments of the present disclosure.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

Various aspects of the present disclosure will be described herein with reference to drawings that may be schematic illustrations of idealized configurations.

The instrument discussed below can be used to quickly and efficiently reduce connecting rods during spinal fusion procedures utilizing pedicle screws and connecting rods. Spinal surgeons need rod reduction instruments that can quickly engage connecting rods, provide mechanical advantage when needed, and have mechanical mechanisms to ensure ease of removal at completion of the procedure. Rod reduction instruments can utilize threaded shafts to provide mechanical advantage to reduce connecting rods through rotation of an instrument handle or tool, such as a T-handle; a hex wrench, a screwdriver, or other tool with a common or proprietary bit; or the like. However, reduction instruments that solely utilize threaded reduction can slow down spinal procedures and require too much manipulation to first engage the rod. Ratchet mechanisms can be utilized to reduce the time and effort to make initial engagement of a connecting rod, but ratchet mechanisms can jam during use and cause difficulties in completing a procedure. In extreme cases, jammed instruments can require cutting the connecting rod and removing the pedicle screw. The present disclosure is directed to various ratchet lock-out mechanisms for use in rod reduction instruments to solve the problem of jammed instruments and still provide all the benefits of instruments with ratcheting capabilities.

Rod reduction instruments are typically provided as part of a fixation system that includes implants (pedicle screws), various length connecting rods, and various instruments for the procedure. The instruments can include tools for pedicle targeting, pedicle preparation, screw insertion, rod and closure top insertion, and manipulation. Manipulation tools include rod reduction instruments, such as rod rockers and reducers. The instruments discussed herein are variations of axial reducers, but the ratchet lock-out mechanisms and techniques could be implemented on other rod reduction instruments utilizing a threaded shaft. Commercial examples of axial reducers include reduction instruments provided by Zimmer Biomet as part of the Vital™ Spinal Fixation System. Commercial examples of rocket reducers include reducers provided by Zimmer Biomet as part of the Polaris™ or Lineum® OCT spinal deformity correction systems. Surgical technique guides from Zimmer Biomet, for systems such as the Vital™ Spinal Fixation System, provide an excellent overview of reduction instrument use and interactions with pedicle screw implants and connecting rods. Accordingly, details regarding how these instruments connect with the implants and operate are not discussed in detail, accept as needed to under the features and aspects of the present disclosure discussed herein.

FIG. 1A is an isometric view of a rod reduction instrument 100, in accordance with example embodiments of the present disclosure. The rod reduction instrument 100 can include an inner sleeve 101 and an outer housing 110. The distal end of the inner sleeve 101 can include engagement members 103, which are adapted to engage a housing on a pedicle screw that receives a connecting rod. The outer housing 110 can include a top sleeve 115 (or first housing portion 115) rotationally coupled to a bottom sleeve 111 (or second housing portion 111). The top sleeve 115 can include a tool socket 116 and a ratchet mechanism 120. The distal end of the bottom sleeve 111 can include a rod engagement 112, which in this example is a cut-out (e.g., semi-circular, or generally configured to conform to an edge or surface of a connecting rod) in opposing sides of the distal end. In operation, the outer housing 110 translates over the inner sleeve 101, after the inner sleeve 101 is coupled to the pedicle screw head via engagement members 103. It is noted that "inner sleeve" and "inner shaft" may be considered equivalent, for purposes of the present disclosure. The top sleeve 115 may be rotatably coupled to the bottom sleeve 111 and adapted to convert rotational input into linear translation of the outer housing 110 relative to the inner sleeve 101.

The rod reduction instrument 100 is an example of a tower reducer that incorporates the ratchet lock-out mechanism to enable two different reduction modes of operation. First, with the ratchet mechanism operation, the tower reducer operates in a quick on, quick off mode that captures the screw head and engages the rod more quickly. After coupling the engagement members 103 of the inner sleeve 101 to a head of a pedicle screw, the outer housing 110 can slide over the inner sleeve 101 until the rod engagement 112 engages the rod. A fine-tuning operation may include attaching a tool (a T-handle; a hex wrench, a screwdriver, or other tool with a common or proprietary bit; or the like) to the tool socket 116 to rotate the top sleeve 115 causing the outer housing 110 to translate further downward reducing the rod into the head of the pedicle screw. For instance, reduction using the tool socket 116 is accomplished by an engagement feature of the ratchet mechanism 120 engaging a proximal portion of the inner sleeve 101. In an example, the engagement feature can be a threaded portion of the ratchet mechanism 120. In other examples, the engagement feature can be an alternative structure, such as small protrusions (numbs) or detents with captured ball bearings. It is noted the fine-tuning operation may be manually actuated or adjusted without departing from the scope of the present disclosure.

The ratchet mechanism, discussed in greater detail below, can be temporarily disengaged through activation of a button or switch, which allows for a smooth and quick initial engagement of the connecting rod. In some examples, the button or switch on the ratchet mechanism 120 needs to be activated to allow the outer housing 110 to disengage and freely translate over the inner sleeve 101. In other examples, the ratchet mechanism 120 allows the engagement feature to bypass or skip over the threads on the proximal section of the inner sleeve 101 without activation of the button on the ratchet mechanism.

In this example, the ratchet mechanism 120 can be shifted into a fixed mode or a fine-tuning operation and/or a threaded mode of operation, locking out the ratchet mechanism. As discussed in detail below, locking out the ratchet mechanism 120 involves forcing an engagement feature of the ratchet mechanism 120 into fixed engagement with a threaded portion of the inner sleeve 101. In this fixed mode, the reducer operates as a threaded reduction instrument, with no rapid translation of the outer housing 110. Accordingly, in the fixed mode the outer housing 110 translates based solely on rotation input received through the tool socket 116 (or any rotation of the top sleeve 115 portion of the outer housing 110). Shifting the ratchet mechanism 120 of the rod reduction instrument 100 into fixed mode enables a user to remove the rod reduction instrument 100 from difficult reduction scenarios, where a ratcheting reduction instrument may not function properly due to high reduction forces. For example, because ratcheting instruments typically rely upon some form of biasing element, such as a coil spring, to keep a threaded member engaged with the threaded inner sleeve, in certain situations the coils spring can fail to keep the threads engaged sufficiently to overcome forces operating on the instrument. In these situations, a ratcheting only instrument may have to be removed through extraordinary measures, such as cutting the connecting rod and removing the pedicle screw. A dual mode ratchet mechanism with a lock-out capability can avoid such extraordinary measures by providing a mechanism to fix engagement of the engagement feature of the ratchet mechanism 120 against the threaded portion of the inner sleeve 101. In the fixed engagement mode, the rod reduction instrument 100 can leverage the mechanical advantage of the threads to overcome external forces jamming the rod reduction instrument 100.

Figure 1B:
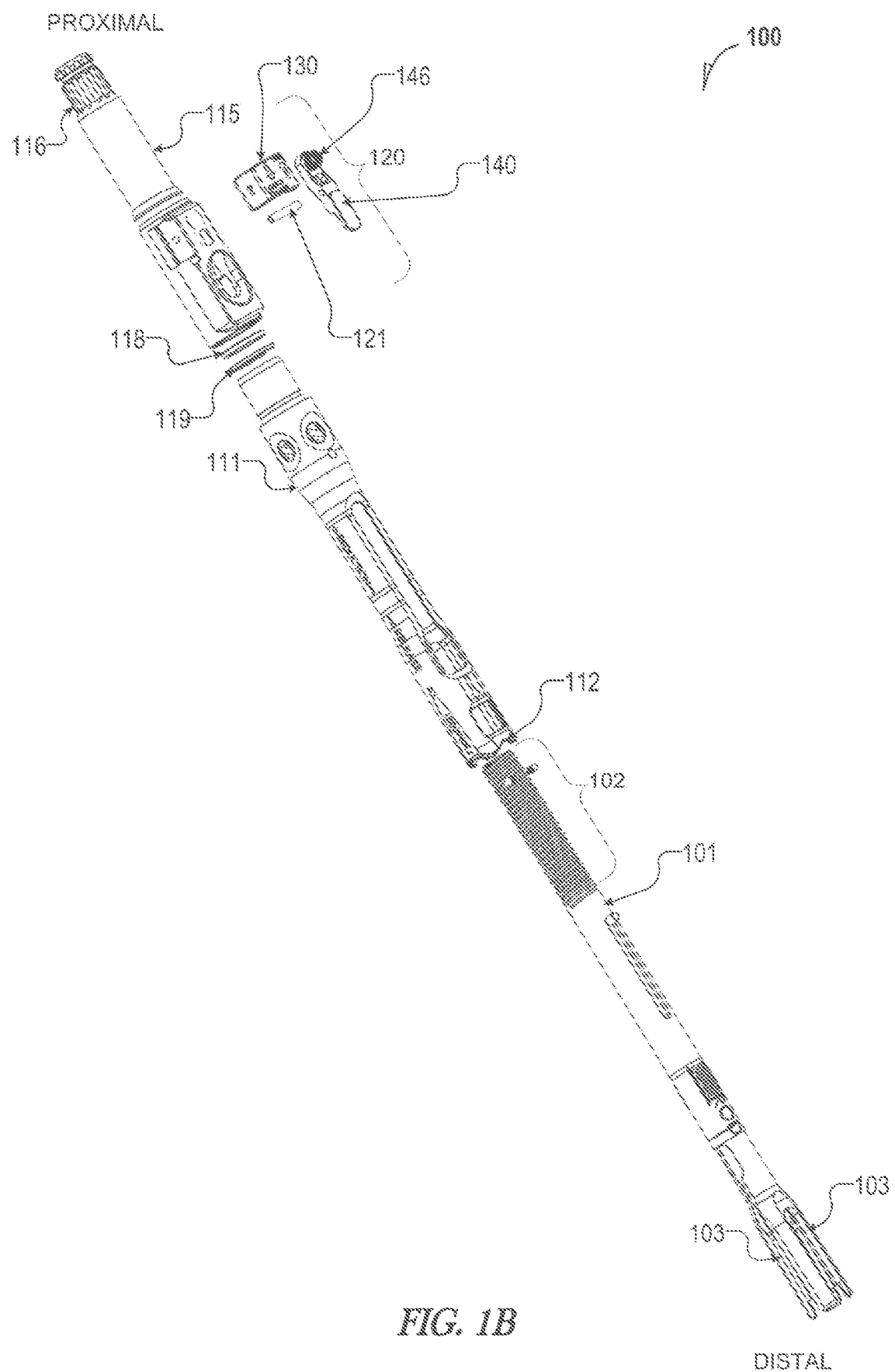
FIG. 1B is an exploded isometric view of the rod reduction instrument of FIG. 1A, in accordance with example embodiments of the present disclosure.

FIG. 1B is an exploded isometric view of the rod reduction instrument 100 introduced above. The exploded view provides an introduction to additional elements of an example ratchet mechanism as well as the overall instrument in accordance with the examples. The rod reduction instrument 100 can include an inner sleeve 101, a threaded proximal portion 102 of the inner sleeve 101, and a plurality of engagement members 103 (collectively referenced as engagement members 103). The rod reduction instrument 100 can also include an outer housing that includes a top sleeve 115 that rotates in reference to a bottom sleeve 111. The top sleeve 115 is coupled to the bottom sleeve via a thrust washer 118 and retaining ring 119. In this example, the ratchet mechanism 120 can include a pivot pin 121, a locking mechanism 130, a lever member 140, and a biasing member 146.

Figure 2:
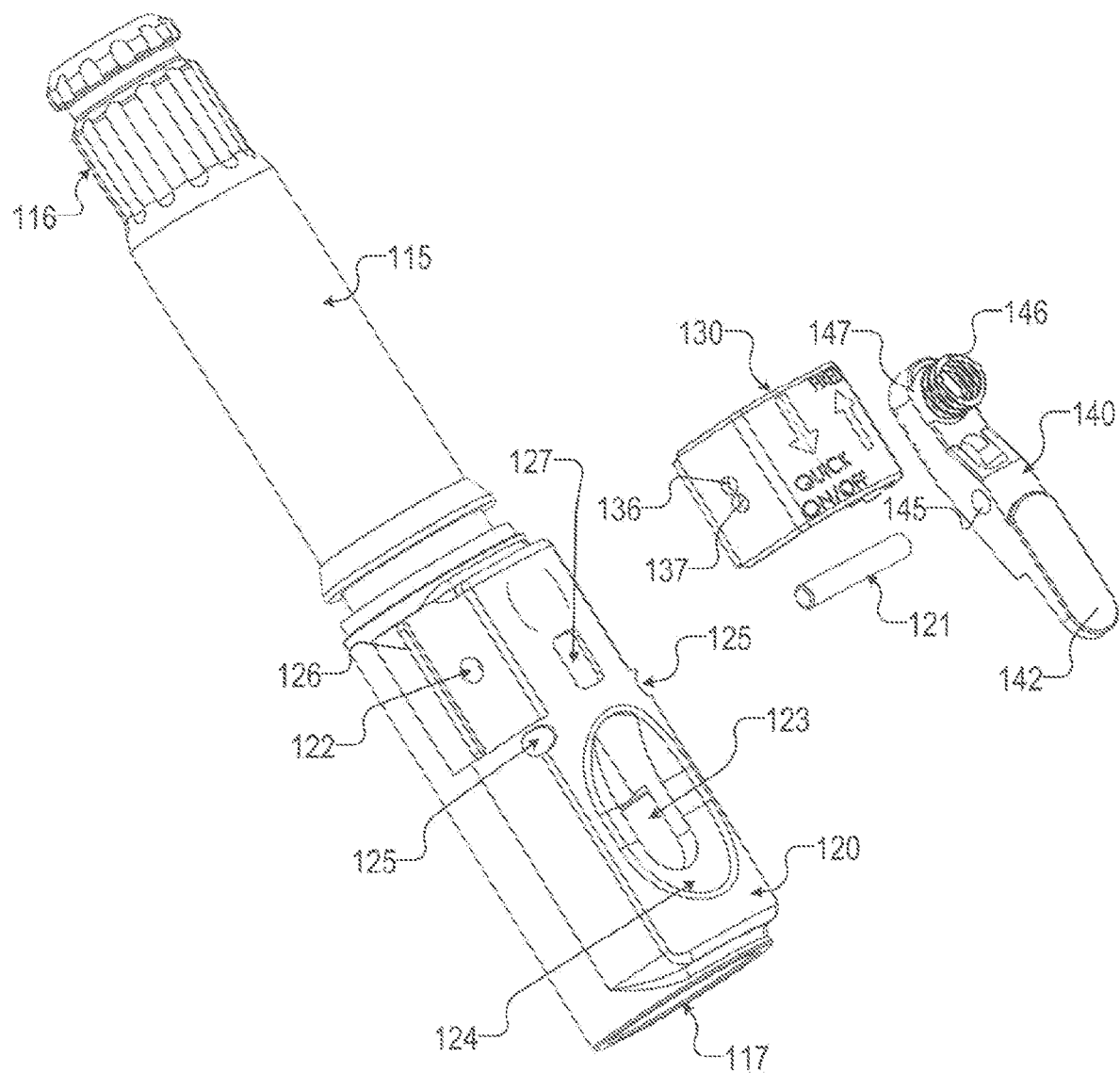
FIG. 2 is an exploded isometric view of an upper section of the rod reduction instrument of FIG. 1A, in accordance with example embodiments of the present disclosure.

FIG. 2 is an exploded isometric view of an upper section of a rod reduction instrument 100, in accordance with example embodiments of the present disclosure. In this example, the top sleeve 115 and the ratchet mechanism 120 of the rod reduction instrument 100 are illustrated in additional detail. The ratchet mechanism 120 includes features built into the top sleeve 115, such as a detent bore 122, a button opening 123, a button cutout 124, pivot pin bores 125, slide lock rails 126, and a transverse pin opening 127. FIG. 2 also illustrates the top sleeve 115 with a tool socket 116 and rotational coupling 117. The rotational coupling 117 is where the top sleeve 115 is connected to the bottom sleeve 111. The ratchet mechanism 120 also includes a pivot pin 121, a locking mechanism 130, a lever member 140, and a biasing member 146. The locking mechanism 130 can also include a lock detent 136 and a ratchet detent 137, which operate to retain the locking mechanism 130 is one of the two modes (locked or fixed and ratcheting). The lever member 140 can include a ratchet release button 142, a pivot 145, and a bias recess 147. The pivot 145 can receive the pivot pin 121 and is where the lever member 140 rotates or pivots in ratcheting mode. The biasing member 146 operates to bias the lever member 140 into engagement with the threaded proximal portion of the inner sleeve 101. As illustrated in greater detail in FIGS. 3A-3J, the biasing member 146 can be a wave washer spring but can also be a coil spring or other comparable biasing member. In certain examples, an elastic or elastomeric material could be substituted for the wave washer spring. The biasing member needs to allow for sufficient travel to clear threaded on the inner sleeve, with provide a balance between thread engagement and ratcheting motion.

The locking mechanism 130 slides on the slide lock rails 126 when assembled into the ratchet mechanism 120. The detent bore 122 is designed to hold a detent ball to engage the lock detent 136 and ratchet detect 137 when locking mechanism 130 slides between fixed mode and ratcheting mode (also referred to as Quick On/Off mode).

Figure 3A:
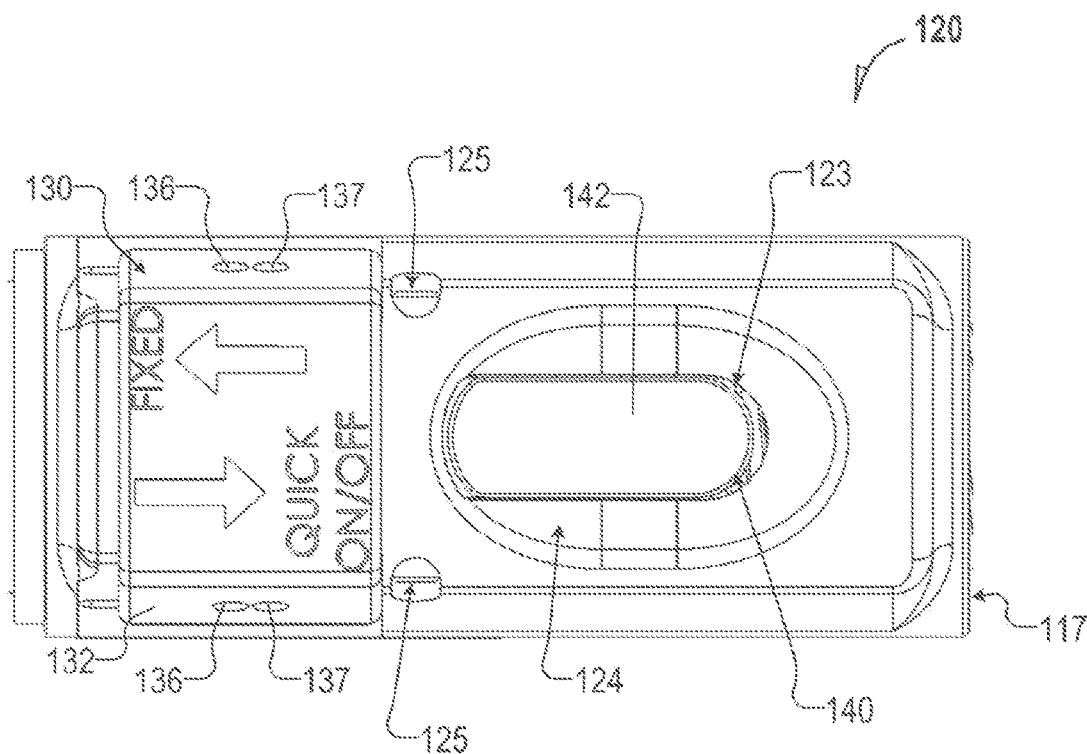
FIGS. 3A-3J are diagrams and drawings of a ratchet mechanism used in the rod reduction instrument of FIG. 1A, in accordance with example embodiments of the present disclosure.

FIGS. 3A-3J are diagrams and drawings of a ratchet mechanism used in a rod reduction instrument, in accordance with example embodiments of the present disclosure. FIG. 3A is a drawing of a superior surface of an assembled the ratchet mechanism 120. In this example, the ratchet mechanism 120 can include a button opening 123, button cutout 124, pivot pin bores 125, a locking mechanism 130, lever member 140, and ratchet release button 142. The locking mechanism in this example includes a slide lock 132. In one non-limiting example, the slide lock 132 may be a U-shaped linear slide that is further illustrated in the following figures. In this example, the lock detent 136 and ratchet detent 137 are shown on opposing arms of the U-shaped slide lock 132.

Figure 3B:
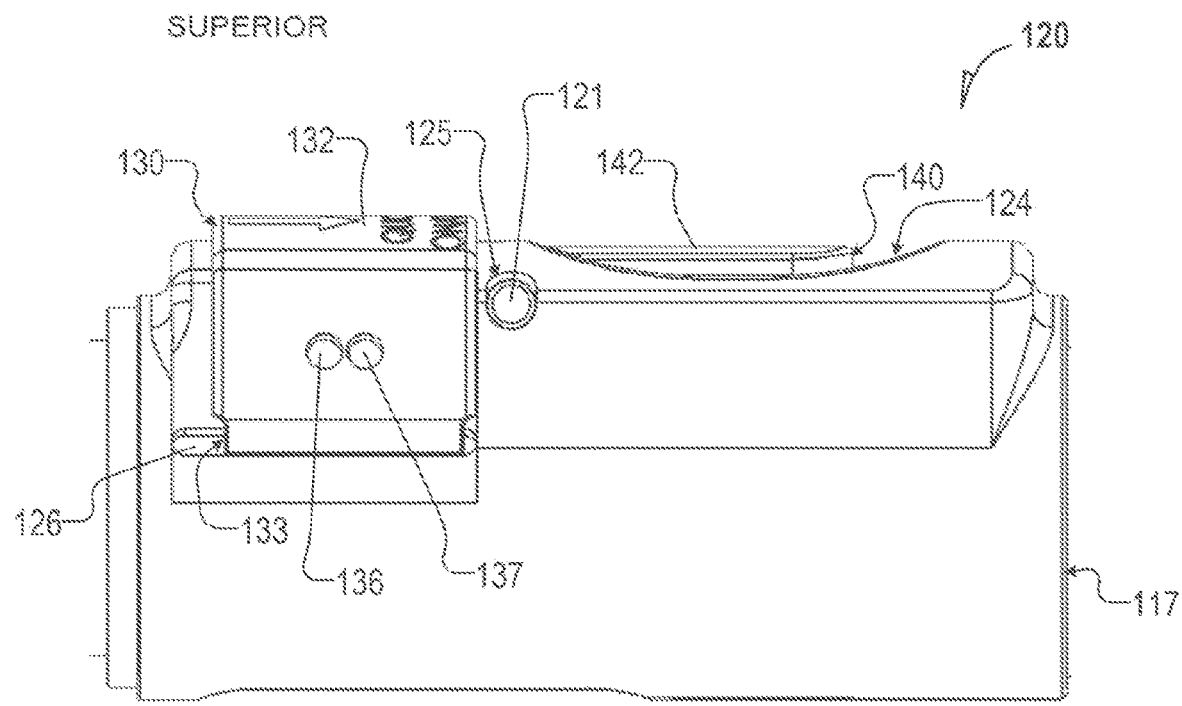

FIG. 3B is a drawing of a lateral side of the ratchet mechanism 120. In this view, the slide lock 132 is illustrated as being engaged with one of the slide lock rails 126 along a slide recess 133. The slide lock 132 includes a slide recess 133 along the outbound edge of each arm of the structure. Also illustrated in this view is the pivot pin 121 within the pivot pin bore 125. When the ratchet release button 142 of the lever member 140 is activated, the lever member 140 pivots on the pivot pin 121 and the engagement feature 141 disengages from a threaded portion of the inner sleeve 101.

Figure 3C:
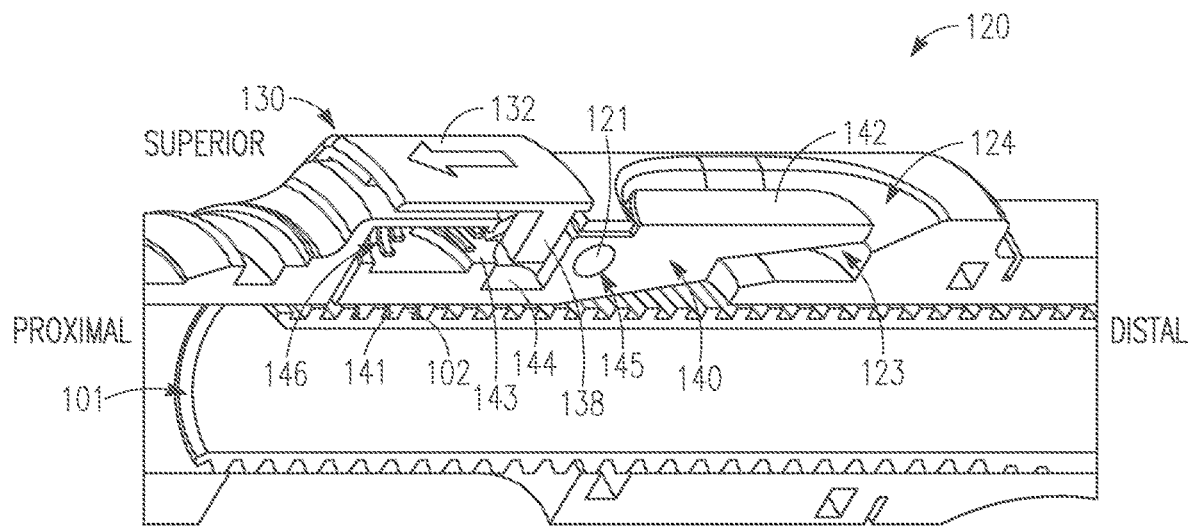
Figure 3D:
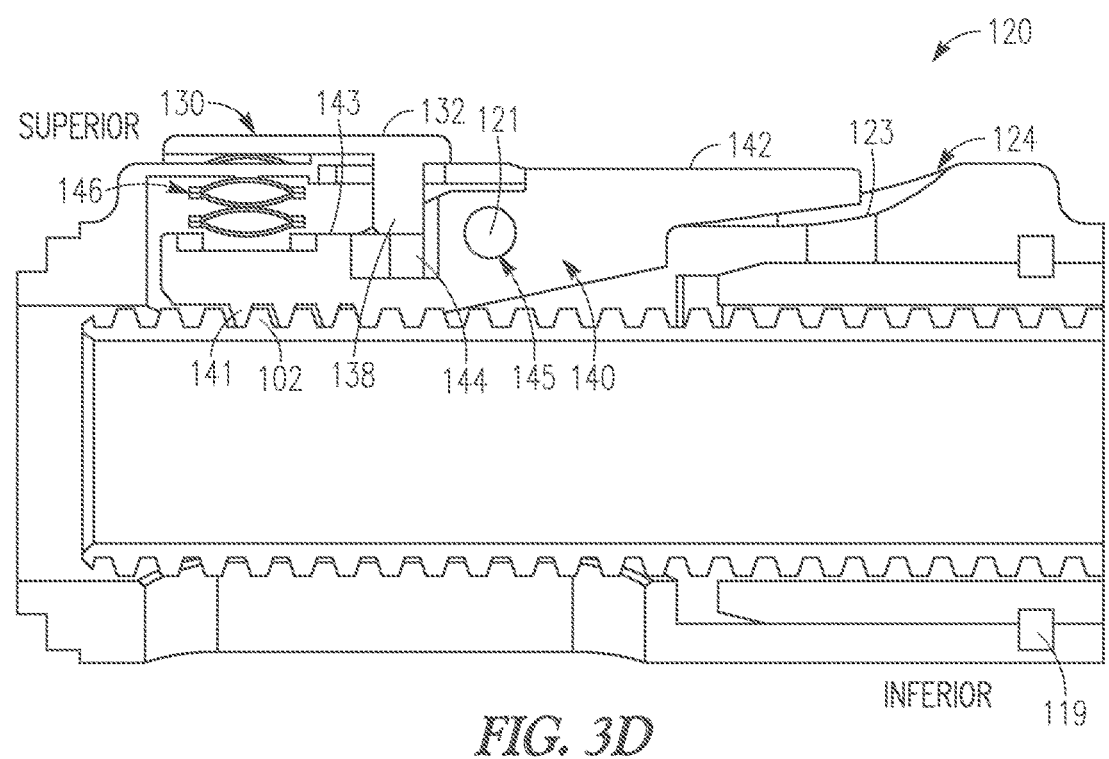

FIGS. 3C-3D are cutaway views of the ratchet mechanism 120 and associated portions of the inner sleeve 101. In these views, the following ratchet mechanism 120 details are depicted, pivot pin 121, button opening 123, button cutout 124, slide lock 132, lever member 140, and biasing member 146. In this example, the slide lock 132 includes the transverse pin 138, which is the structure of the locking mechanism 130 that locks out the ratcheting action of the lever member 140. In these views, the lever member 140 is illustrated as including an engagement feature 141 on an inferior side of the proximal portion. The cutaway demonstrates how the engagement feature 141 engages the proximal threaded portion 102 of inner sleeve 101. In this example, the engagement feature 141 is a plurality of partial threads that correspond to the proximal threaded portion 102 of the inner sleeve 101. The cutaway also illustrates how the biasing member 146 biases the engagement feature 141 into engagement with the proximal threaded portion 102. The lever member 140 also includes a locking surface 143 and a ratchet cavity 144, which are positioned below the transverse pin 138 of the slide lock 132. In ratcheting mode, the slide lock 132 is positioned as shown and the transverse pin 138 is opposite the ratchet cavity 144, which provides clearance for the lever member 140 to pivot without interference from the transverse pin 138. However, in the fixed (or locked) mode, the slide lock 132 is shifted proximally, and the transverse pin 138 is positioned opposite the locking surface 143. In the fixed mode, the lever member 140 is prevented from pivoting due to engagement between the transverse pin 138 and the locking surface 143.

Figure 3E:
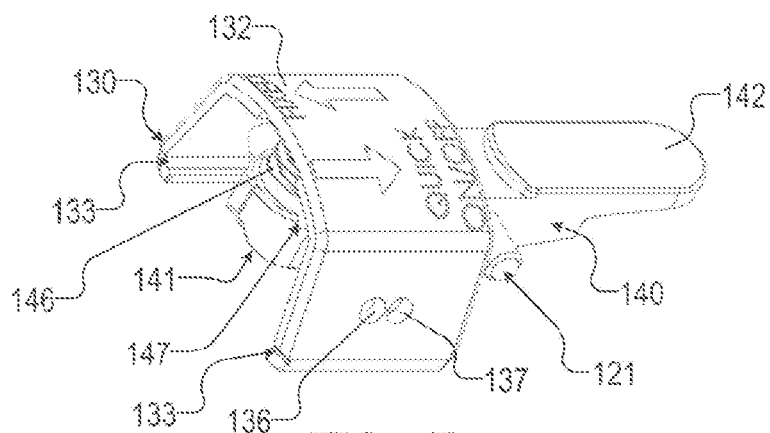
Figure 3F:
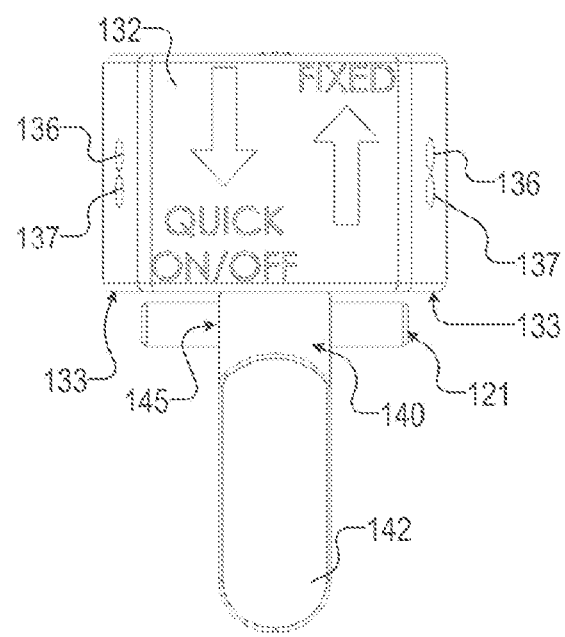
Figure 3G:
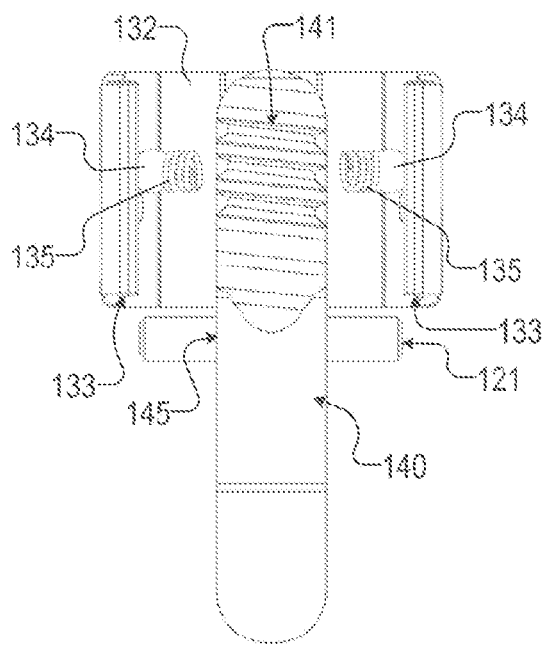
Figure 3H:
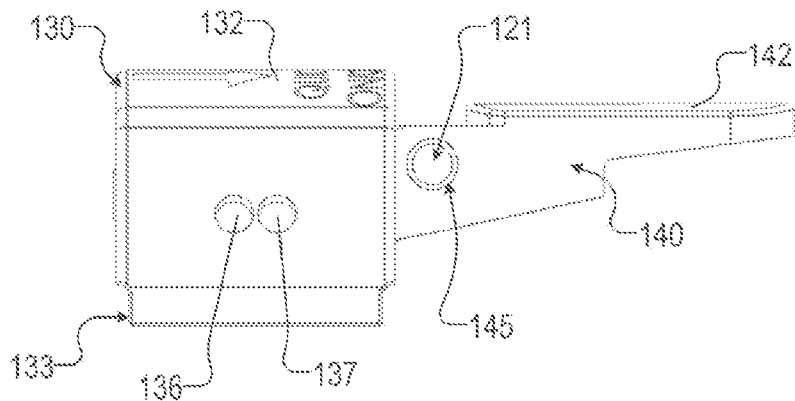
Figure 3I:
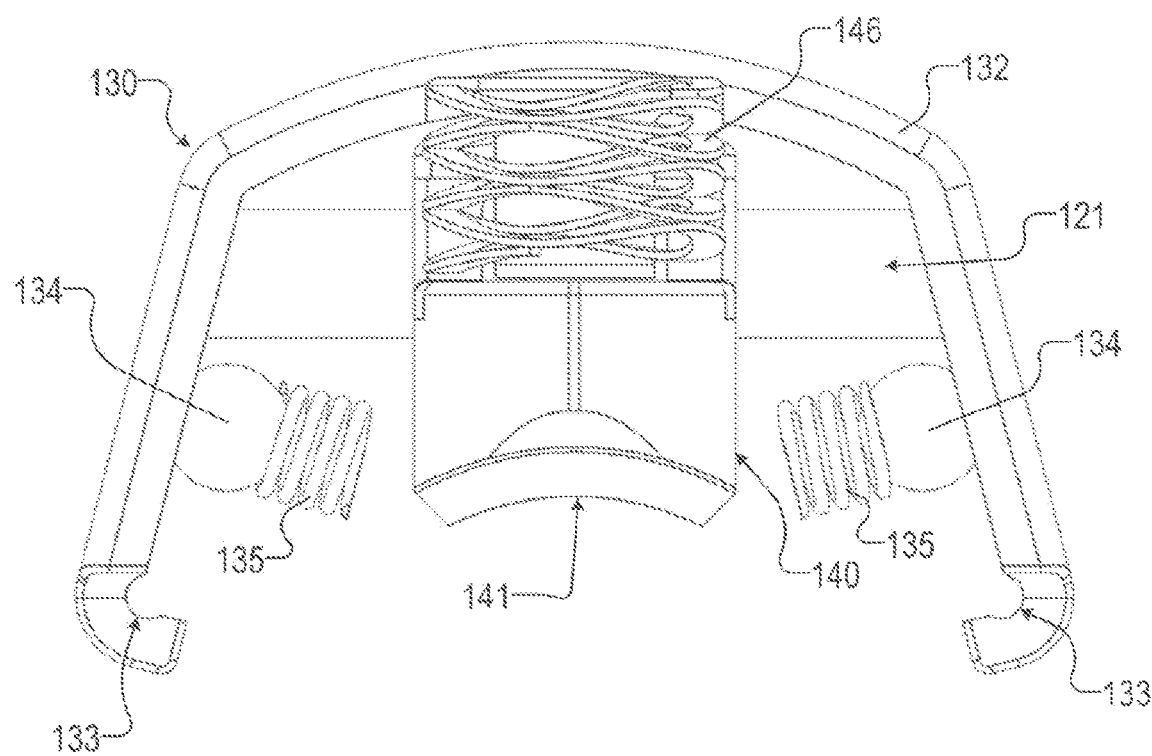
Figure 3J:
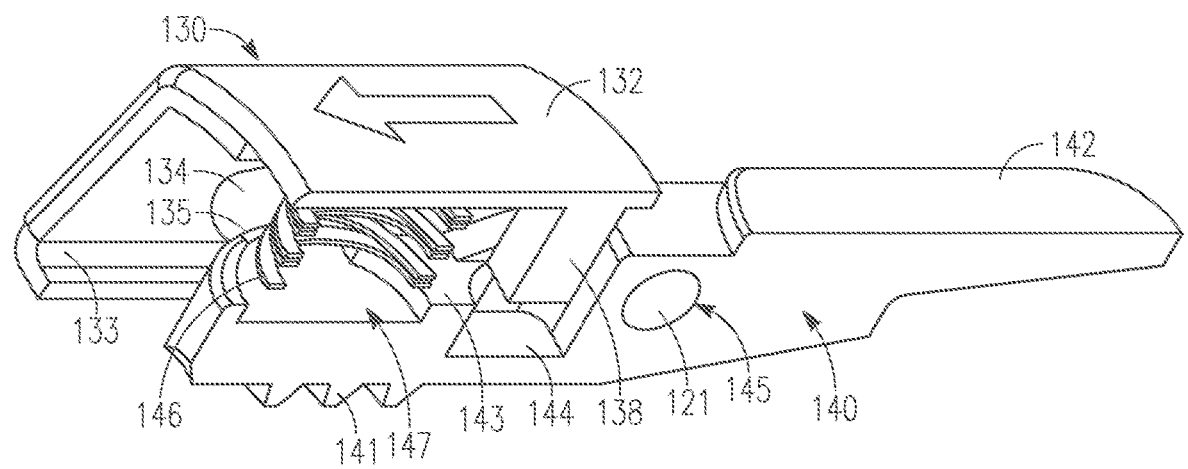

FIGS. 3E-3J are various drawings providing additional detailed views of the locking mechanism 130, the lever member 140, and parts of the ratchet mechanism 120. FIG. 3E is an isometric view of the pivot pin 121, locking mechanism 130, and lever member 140. In this view, the structure of the slide lock 132 is depicted with the slide recesses 133 along the ends of each arm. In one non-limiting example, the structure of the slide lock 132 may be U-shaped. FIG. 3F is a superior surface view of the locking mechanism 130 and lever member 140. FIG. 3G is an inferior surface view of the locking mechanism 130 and lever member 140. In this view, the engagement feature 141 of the lever member 140 is shown including at least three angled threads in the thread pattern. In other examples, a different thread pattern can be utilized and the engagement feature 141 can have more or fewer threads. In other examples, the engagement feature 141 can include a series of protrusions positioned to engage the threaded proximal portion 102. In yet other examples, the engagement feature 141 can include one or more detents with captured ball bearings positioned to engage the threads in the threaded proximal portion 102. For instance, the threads in the threaded proximal portion 102 may be structured to accept the ball bearings. This view also includes detent balls 134 and detent springs 135, which assist in holding slide lock 132 in the fixed or ratcheting position. FIG. 3H is a lateral view drawing of the locking mechanism 130 and lever member 140. FIG. 3I is an axial view along a longitudinal axis of the rod reduction instrument of the locking mechanism 130 and the lever member 140. This view depicts the structure of the slide lock 132 with the slide recesses 133. In one non-limiting example, where the structure of the slide lock 132 is U-shaped, the slide recesses 133 may be c-shaped and may be positioned on the outbound end of each leg of the U. The view also depicts the curve of the engagement feature 141 on the inferior side of the proximal portion of the lever member 140. Opposite the engagement feature 141 is the biasing member 146, which is held in place by an inferior surface of the slide lock 132. FIG. 3J is a cutaway perspective view of the locking mechanism 130 and lever member 140 providing a slightly different perspective on the elements discussed above.

Figure 4:
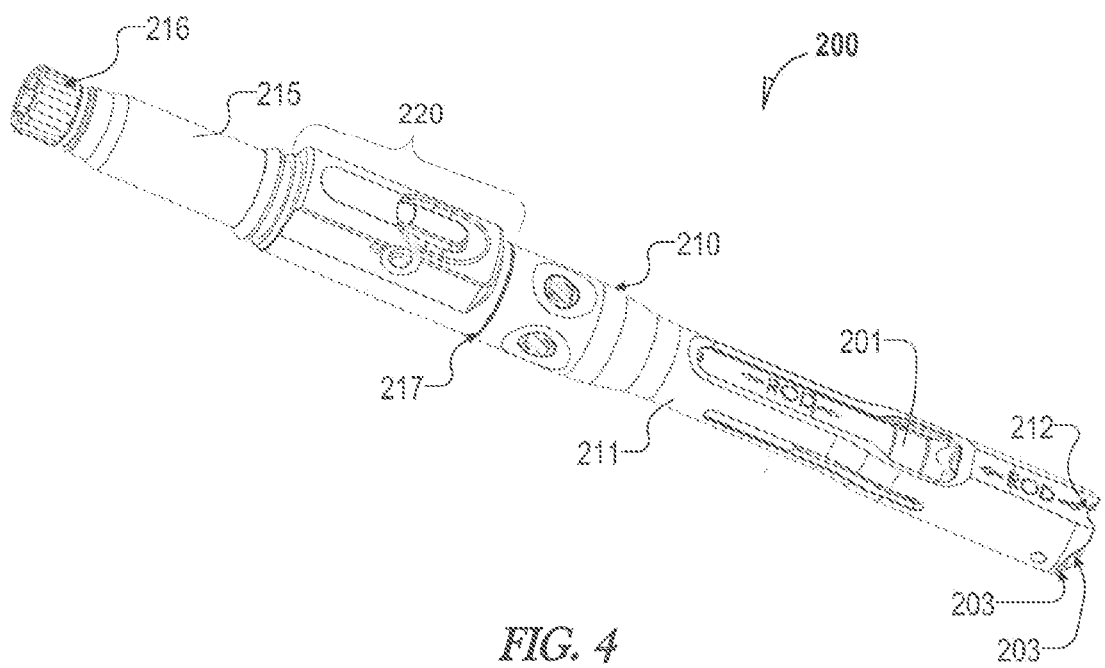
FIG. 4 is an isometric view of a rod reduction instrument, in accordance with example embodiments of the present disclosure.

FIG. 4 is an isometric view of a rod reduction instrument 200, in accordance with example embodiments of the present disclosure. The rod reduction instrument 200 is similar to rod reduction instrument 100 discussed above but includes a different ratchet lock-out mechanism. The following discussion will primarily focus on the differences in the ratchet mechanism 220, as the rest of the functionality of the rod reduction instrument 200 is comparable to that of rod reduction instrument 100. As such, embodiments directed to the rod reduction instrument 100 may be directed to the rod reduction instrument 200, and vice versa, unless otherwise noted.

As illustrated in FIG. 4, the rod reduction instrument 200 can include an inner sleeve 201, engagement members 203, an outer housing 210, and a ratchet mechanism 220. The outer housing 210 can include a bottom sleeve 211 and a top sleeve 215. The top sleeve 215 can include a tool socket 216, which can be used to receive a handle to introduce rotation to the top sleeve 215. The top sleeve 215 can rotate in reference to the bottom sleeve 211 around the rotational coupling 217. The bottom sleeve 211 includes a rod engagement 212 on a distal end. It is noted that "inner sleeve" and "inner shaft" may be considered equivalent, for purposes of the present disclosure.

Figure 5:
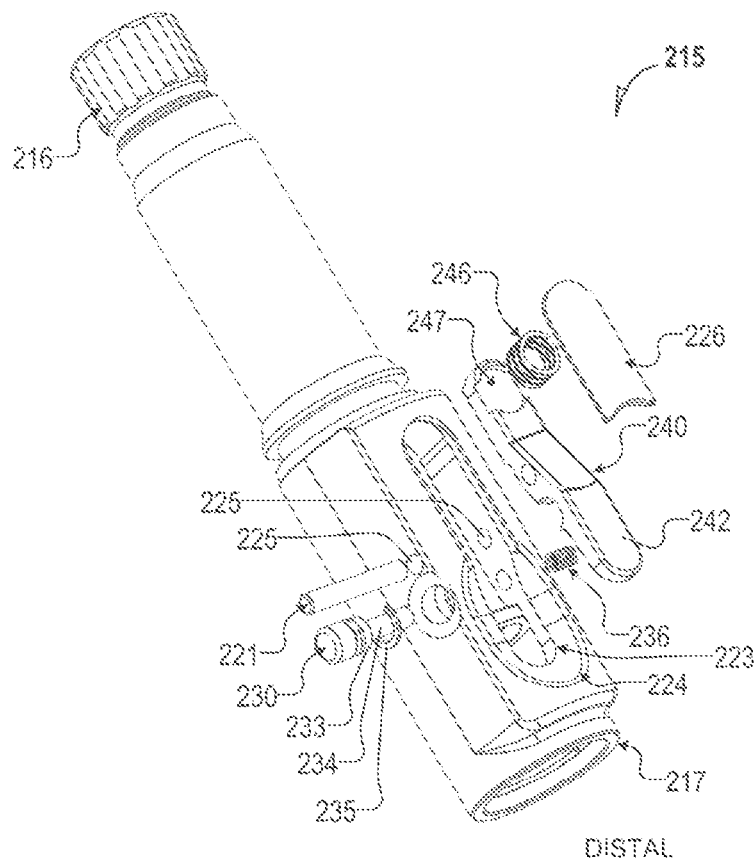
FIG. 5 is an exploded isometric view of an upper section of a rod reduction instrument of FIG. 4, in accordance with example embodiments of the present disclosure.

FIG. 5 is an exploded isometric view of an upper section (top sleeve 215) of the rod reduction instrument 200, in accordance with example embodiments of the present disclosure. In this example, the ratchet mechanism 220 includes a pivot pin 221, a button opening 223, a button cutout 224, pivot pin bores 225, a ratchet cover 226, a locking mechanism 230, and a lever member 240. The lever member 240 is similar to the lever member 140 and includes a threaded inferior surface on a proximal portion and a ratchet release button 242 on a superior surface of a distal portion. The lever member 240 receives the pivot pin 221 between the proximal portion and distal portion. On a superior surface of the proximal portion of the lever member 240 there is a bias recess 247 adapted to receive a biasing member 246. In this example, the locking mechanism 230 includes a slide lock 232 in the form of a stepped cylindrical shaft. The slide lock 232 includes a large diameter section 233, a small diameter section 234, a locking ring 235, and a biasing member 236. As assembled, the slide lock 232 is located within a slide lock bore 237 (labeled in FIG. 6J), with the locking ring 235 securing the slide lock 232 shaft within the slide lock bore 237.

In this example, the lever member 240 and the biasing member 246 are dropped into the ratchet mechanism 220 through an opening in the superior surface, then the ratchet cover 226 is slid into position over the opening to provide an engagement surface for the biasing member 246 to operate against. In an example, edges of the ratchet cover 226 slide into recesses in the opening in the superior surface of the ratchet mechanism 220. Once the lever member 240 is in position, the pivot pin 221 can be inserted to retain the lever member 240, while allowing the lever member 240 to pivot.

In this example, the ratchet mechanism 220 can be shifted into a fixed mode or a fine-tuning operation and/or a threaded mode of operation, locking out the ratchet mechanism. As discussed in detail below, locking out the ratchet mechanism 220 involves forcing an engagement feature of the ratchet mechanism 220 into fixed engagement with a threaded portion of the inner sleeve 201. In this fixed mode, the reducer operates as a threaded reduction instrument, with no rapid translation of the outer housing 210. Accordingly, in the fixed mode the outer housing 210 translates based solely on rotation input received through the tool socket 216 (or any rotation of the top sleeve 215 portion of the outer housing 210). Shifting the ratchet mechanism 220 of the rod reduction instrument 200 into fixed mode enables a user to remove the rod reduction instrument 200 from difficult reduction scenarios, where a ratcheting reduction instrument may not function properly due to high reduction forces. For example, because ratcheting instruments typically rely upon some form of biasing element, such as a coil spring, to keep a threaded member engaged with the threaded inner sleeve, in certain situations the coils spring can fail to keep the threads engaged sufficiently to overcome forces operating on the instrument. In these situations, a ratcheting only instrument may have to be removed through extraordinary measures, such as cutting the connecting rod and removing the pedicle screw. A dual mode ratchet mechanism with a lock-out capability can avoid such extraordinary measures by providing a mechanism to fix engagement of the engagement feature of the ratchet mechanism 220 against the threaded portion of the inner sleeve 201. In the fixed engagement mode, the rod reduction instrument 200 can leverage the mechanical advantage of the threads to overcome external forces jamming the rod reduction instrument 200.

Figure 6A:
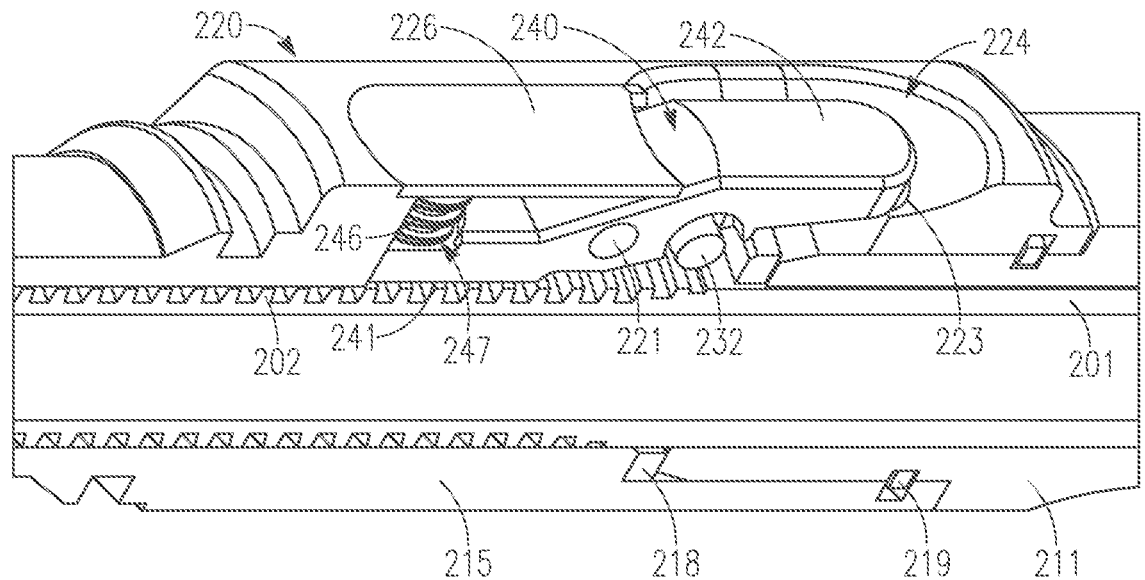
FIGS. 6A-6J are diagrams and drawings of the ratchet mechanism used in the rod reduction instrument of FIG. 4, in accordance with example embodiments of the present disclosure.
Figure 6B:
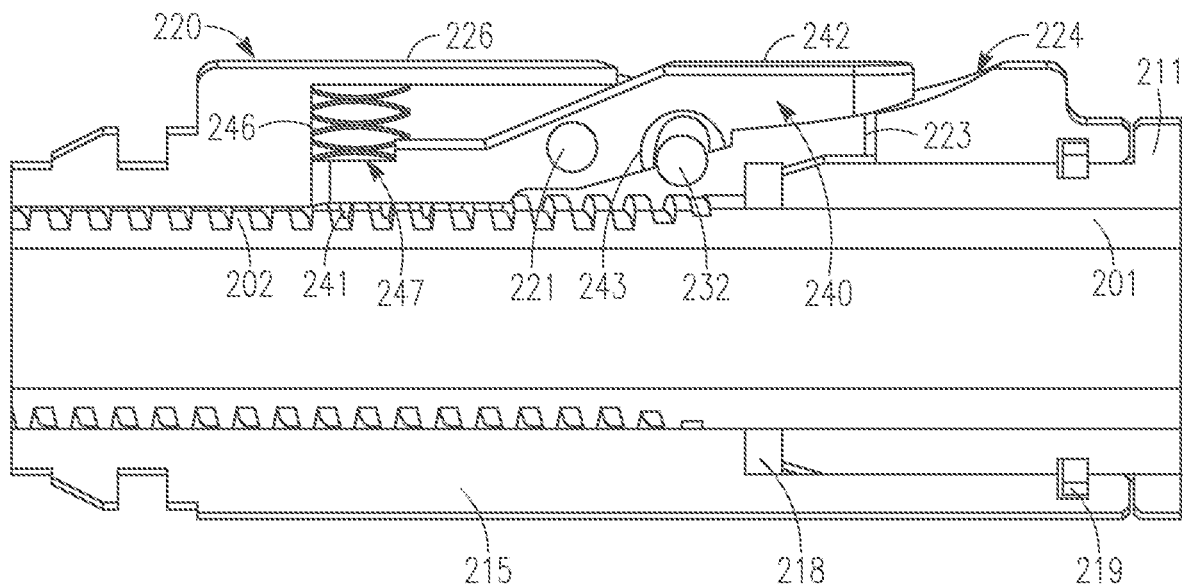

FIGS. 6A-6J are diagrams and drawings of the ratchet mechanism 220 used in the rod reduction instrument 200, in accordance with example embodiments of the present disclosure. FIGS. 6A and 6B are cutaway illustrations of the ratchet mechanism 220 as well as depictions of portions of the inner sleeve 201, top sleeve 215, and bottom sleeve 211. In this example, the thrust washer 218 and retaining ring 219 are illustrated in reference to top sleeve 215 and bottom sleeve 211. Inner sleeve 201 includes a proximal threaded portion 202 which engages with an engagement feature 241 of the lever member 240. The biasing member 246 is illustrated urging the lever member 240 to pivot on a pivot pin 221 and engage the threaded proximal portion 202 of inner sleeve 201. The locking surface 243 is also illustrated in these cutaway views. The locking surface 243 on the lever member 240 is a recess (e.g., semi-circular, or the like) along a lateral inferior surface under a portion of the ratchet release button 242. As illustrated in other figures, the large diameter 233 of the slide lock 232 can be shifted laterally into engagement with the locking surface 243 to prevent the lever member 240 from pivoting and forcing the engagement feature 241 into fixed engagement with the threaded proximal portion 202 of the inner sleeve 201. With the slide lock 232 engaged, the rod reduction instrument 200 operates through rotation of the top sleeve 215 only. The cutaway views also illustrate the structure of the button opening 223 and the button cutout 224. The button opening 223 is an opening in the ratchet mechanism 220 that conforms to the outline of the ratchet release button 242 of the lever member 240, while the button cutout 224 is a recessed portion around the ratchet release button 242. In some examples, the button cutout 224 can include curved sidewalls, and in other examples the sidewalls can be straight but angled.

Figure 6C:
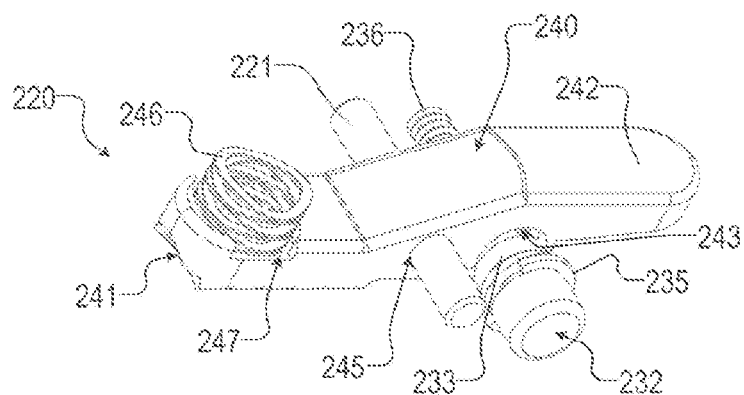

FIG. 6C-6I are various drawings providing additional detailed views of the locking mechanism 230 and lever member 240 parts of the ratchet mechanism 220. FIG. 6C is an isometric view of non-limiting examples of the pivot pin 221, locking mechanism 230, and lever member 240. In the examples, the pivot 245 of lever member 240 is identified as the bore in the lever member 240 receiving the pivot pin 221. Other features of the lever member 240 illustrated in this example include the engagement feature 241, the ratchet release button 242, the locking surface 243, the bias recess 247, and the biasing member 246. The examples illustrate the relationship between the locking surface 243 on the lever member 240 and the large diameter section 233 of the stepped cylindrical slide lock 232. The slide lock 232 includes an enlarged lateral end that operates as a button for activation of the slide lock 232 of the locking mechanism 230.

Figure 6D:
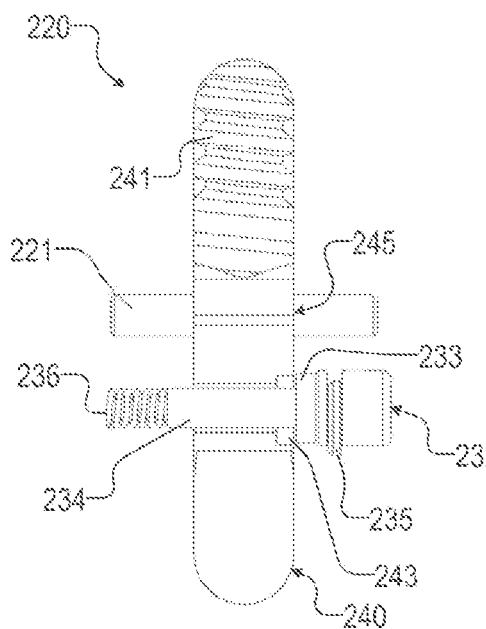

FIG. 6D is an inferior side view of non-limiting examples of the pivot pin 221, locking mechanism 230, and lever member 240. In the examples, the engagement feature 241 of the lever member 240 is illustrated as including at least three threads running at a shallow angle transverse to a longitudinal axis of the lever member 240. In some examples, more or fewer threads can be included on the engagement feature 241. The small diameter section 234 of the slide lock 232 stepped cylindrical shaft is shown within a recess in the inferior side of the ratchet release button 242 portion of the lever member 240. The lock biasing member 236 is illustrated in position to bias the slide lock 232 into an unlocked position.

Figure 6E:
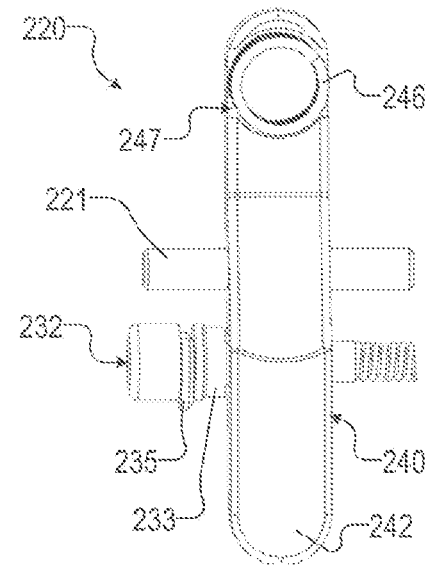
Figure 6F:
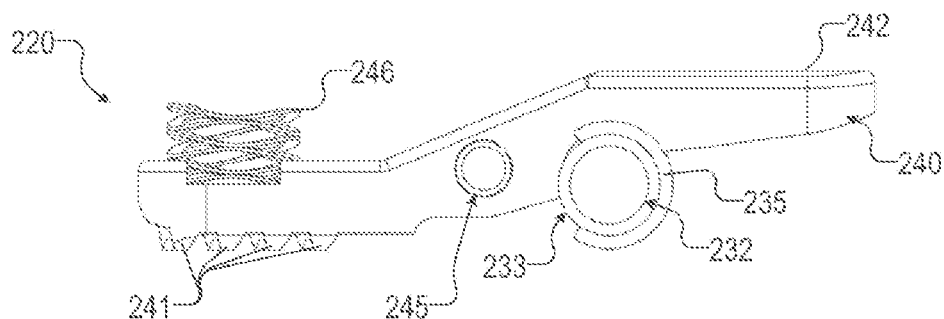

FIG. 6E is a superior side view of the pivot pin 221, locking mechanism 230, and lever member 240. FIG. 6F is a lateral side view of the pivot pin 221, locking mechanism 230, and lever member 240. In the view provided in FIG. 6F, the engagement feature 241 is illustrated as including four partial threads to engage the threaded proximal portion 202 of the inner sleeve 201.

Figure 6G:
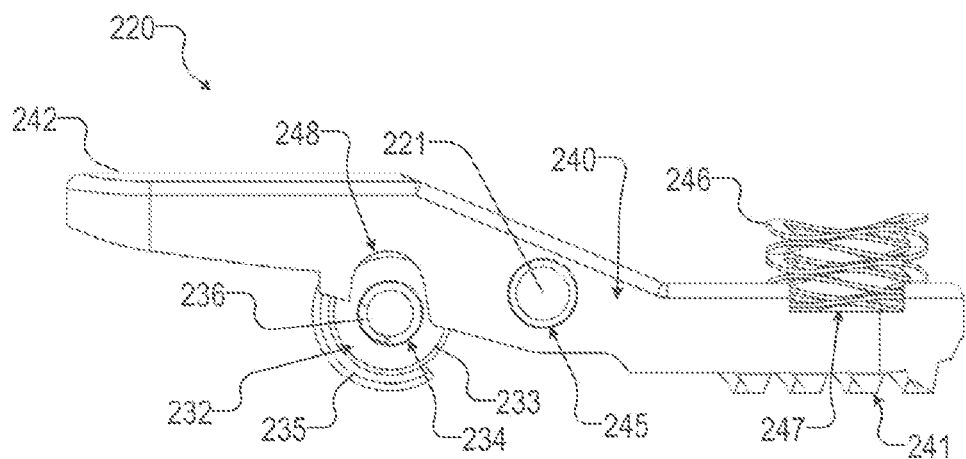

FIG. 6G is a medial side view of the pivot pin 221, locking mechanism 230, and lever member 240. In the view provided in FIG. 6G, the slide lock recess 248 (e.g., U-shaped, or the like) in the inferior side of the ratchet release button 242 portion of the lever member 240 is shown in relationship to the small diameter section 234 and lock biasing member 236 of the slide lock 232. The slide lock recess 248 provides sufficient clearance to allow the lever member 240 to pivot around a pivot pin 221 with the ratchet release button 242 is activated, or when ratcheting as the outer housing 210 slides over the inner sleeve 201.

Figure 6H:
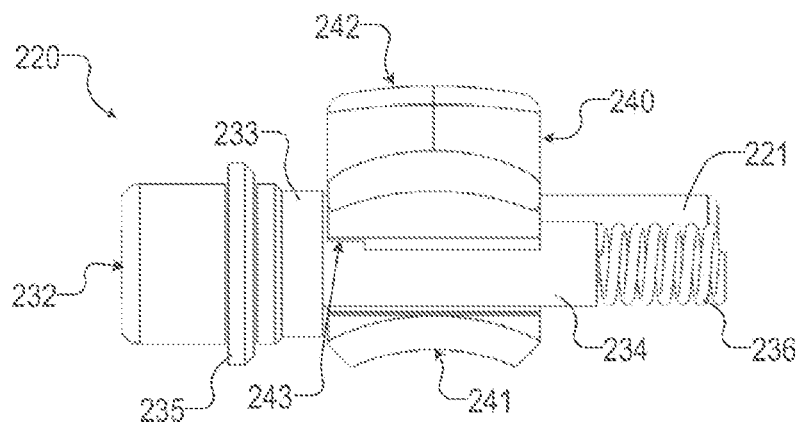
Figure 6I:
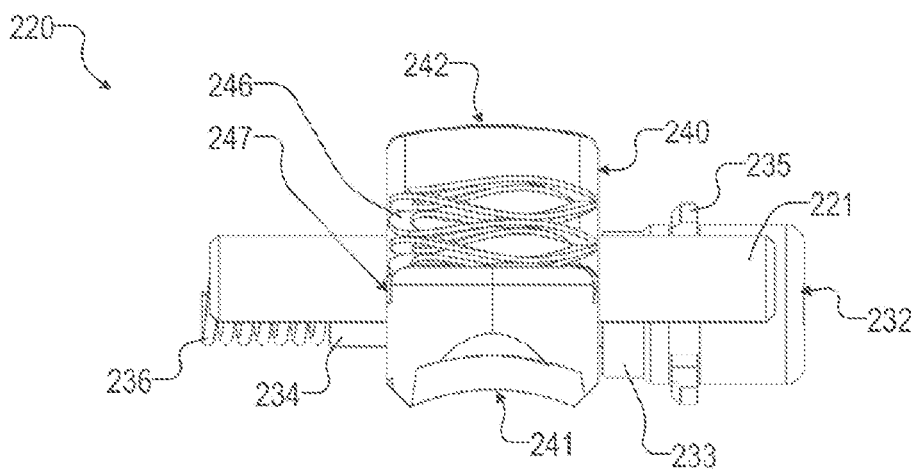

FIGS. 6H and 6I are distal and proximal views, respectively, along the longitudinal axis of the rod reduction instrument 200. FIGS. 6H and 6I depicts the curved structure of the inferior surface of the engagement feature 241 of the lever member 240. The engagement feature 241 is curved to match the outer curvature of the inner sleeve 201.

Figure 6J:
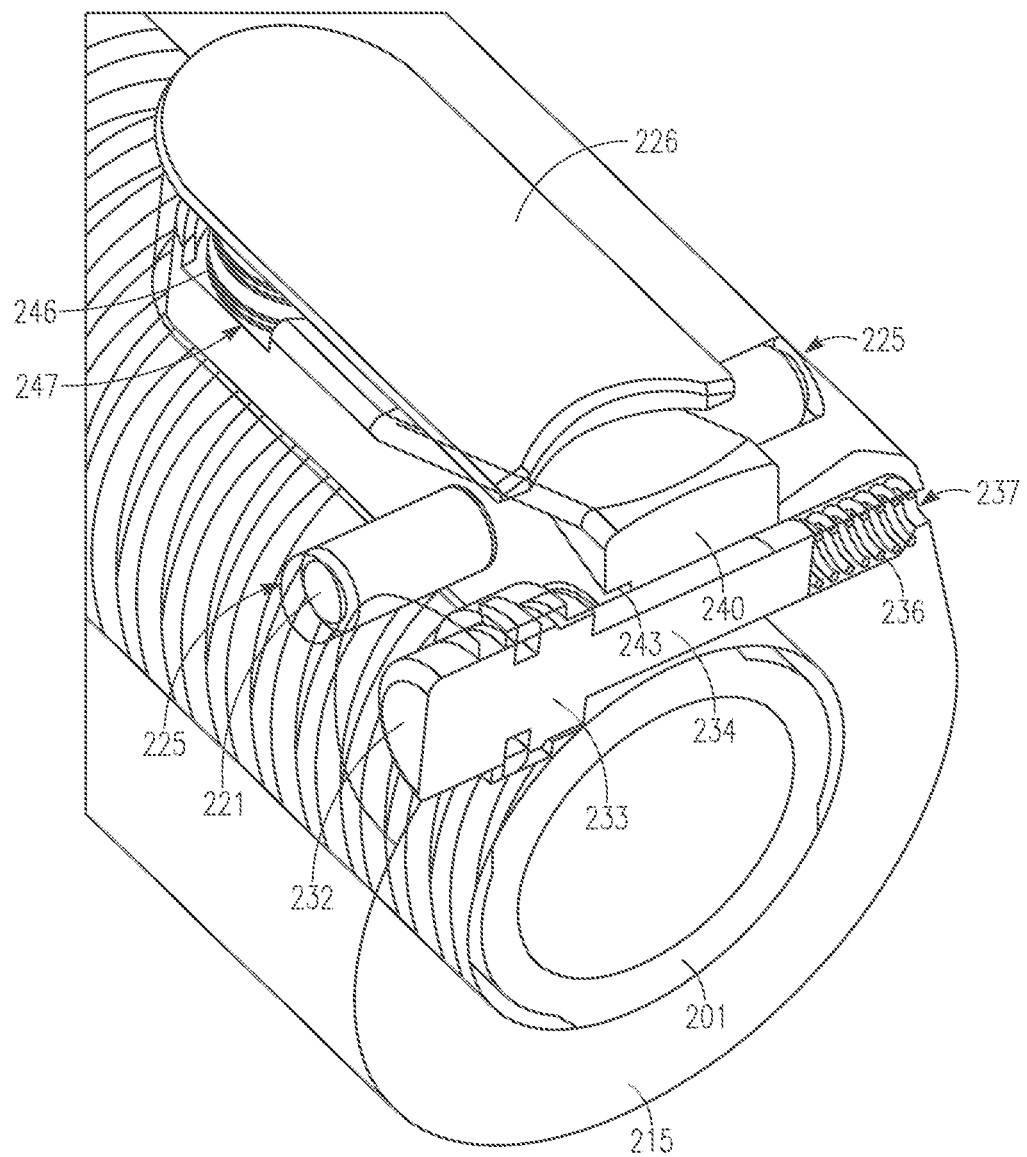

FIG. 6J is a transverse cutaway view of the ratchet mechanism 220, top sleeve 215, and inner sleeve 201. The cutaway runs through the stepped cylindrical shaft of the slide lock 232. As illustrated, the locking ring 235 retains the slide lock 232 within the slide lock bore 237 by engaging a cylindrical recess enlarging a section of the slide lock bore 237. The cutaway also illustrates how the large diameter section 233 can engage the locking surface 243 on the lever member 240 when the button of the slide lock 232 is pushed in compressing the lock biasing member 236.

Figure 7:
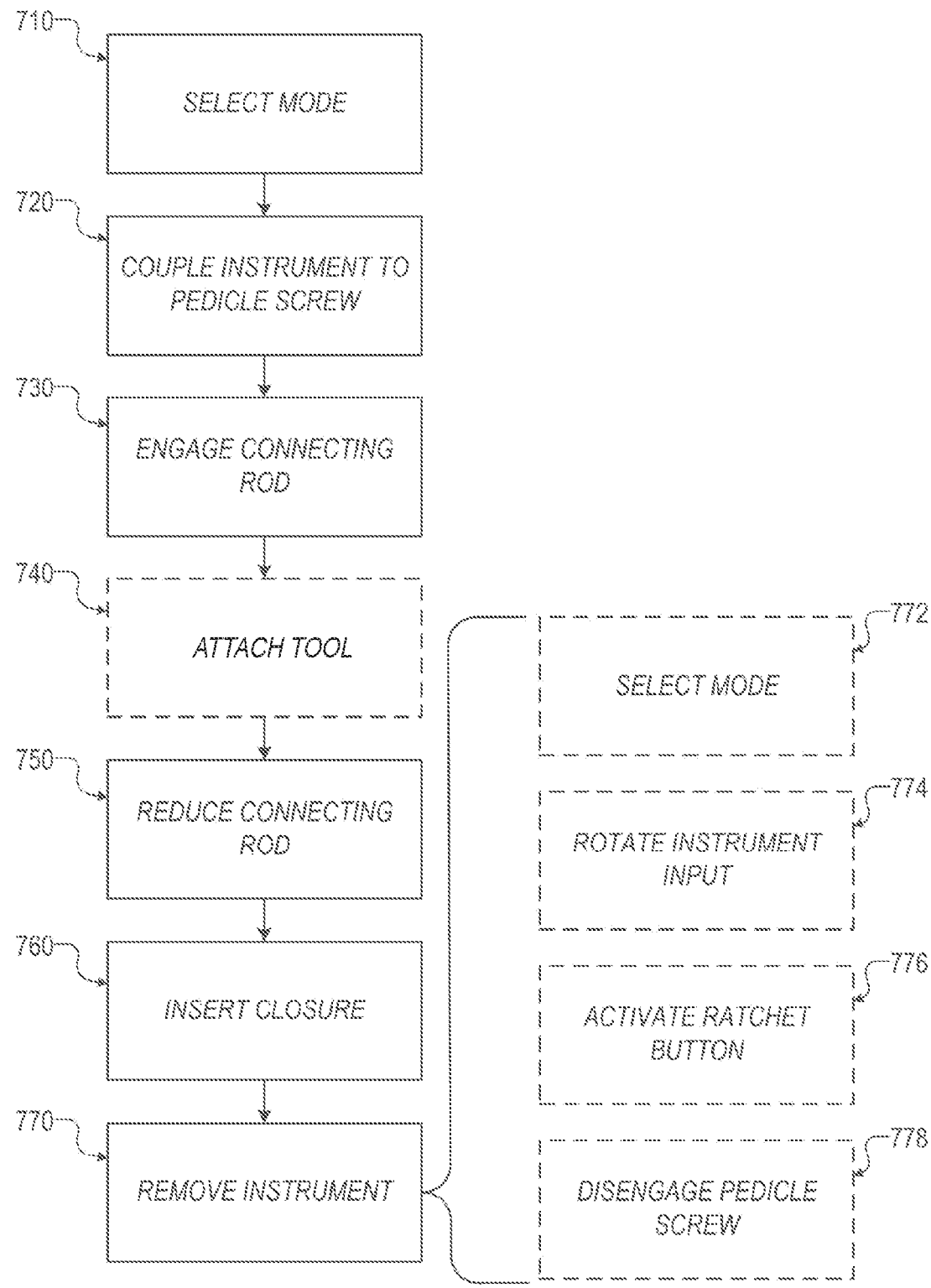
FIG. 7 is a flowchart illustrating a method for using a rod reduction instrument, in accordance with example embodiments of the present disclosure.

FIG. 7 is a flowchart illustrating a method 700 for using a rod reduction instrument, such as the rod reduction instrument 100 or 200 as discussed throughout the present disclosure. In this regard, the steps or processes 700 may cause an adjustment of and/or be performed by the components of the rod reduction instrument 100 or 200. The method 700 illustrates a common set of operations utilizing one of the rod reduction instruments discussed above. However, the method 700 does not cover all possible uses of the instruments, the operations discussed can be done in a different sequence, operations could be repeated or omitted, as fits the particular scenario of use. In this example, the method 700 can include operations such as: selecting Quick On/Off mode or fixed mode at 710, coupling to a pedicle screw at 720, sliding the outer housing into engage with a connecting rod at 730, optionally attaching a tool at 740, reducing the connecting rod at 750, inserting a closure into the pedicle screw at 760, and removing the rod reduction instrument at 770. The operations discussed in method 700 are depicted in a common order of operation, but many of the operations can be shifted into other positions in the method or repeated. For example, the mode of operation can be switched at any point during the procedure.

At 710, the mode of operation of the instrument may being selected. In this example, the Quick On/Off (or ratcheting) mode can be selected by shifting the slide lock, such as slide lock 132, into the Quick On/Off (distal) position. As discussed above, with the instrument in the Quick On/Off mode, the ratchet mechanism is free to ratchet. In other words, the engagement feature 141 of the lever member 140 is not fixed into engagement of the threaded proximal portion 102 of the inner sleeve 101. This allows for a quick or rapid reduction of distance to the pedicle screw. In another example, the user may choose to engage the threaded operation mode by shifting the slide lock into the Fixed (proximal) position. This allows for a fine-tuning of positioning with respect to the pedicle screw.

At 720, the rod reduction instrument may be coupled to a head of a pedicle screw. For example, the engagement members 203 of the rod reduction instrument 100 can be placed into engagement with the head of a pedicle screw. Prior to engaging the pedicle screw, a ratchet release button 142 can be engaged and the inner sleeve 101 can be fully extended into a fully open position. In an example, the instrument can include four separate engagement members that engage four vertical slots on the screw head. In other examples, the instrument may only include two engagement members that engage either arm of the pedicle screw head.

At 730, a connecting rod may be engaged once the head of the pedicle screw is engaged. In this example, the outer housing 110 can slide over the inner sleeve 201 to quickly engage the connecting rod through ratcheting. If the instrument were in the fixed mode, an external force applied (e.g., such as a rotational input) to the top sleeve 115 would be necessary to translate the outer housing 110 over the inner sleeve 101 to engage the connecting rod.

Optionally at 740, a tool may be attached to the tool socket 116 of the top sleeve 115. For example, the tool may include, but is not limited to, a T-handle; a hex wrench, a screwdriver, or other tool with a common or proprietary bit; or the like. It is noted the tool socket 116 may be manually actuated or adjusted, however, without departing from the scope of the present disclosure. It is noted the tool sockets 116, 216 of the respective rod reduction instruments 100, 200 may be actuated via a secondary device including, but not limited to, a robotic arm.

At 750, the rod reduction instrument 100, 200 may be manipulated to reduce the connecting rod into the head of the pedicle screw. Instrument manipulation may include rotation of the tool (or manual actuation of the top sleeve 115 if no extra torque is needed), which causes translation of the outer housing 110. Optionally, the instrument can be shifted into fixed mode if rod reduction is particularly difficult to ensure that the ratchet mechanism 120 does not disengage during threaded reduction.

At 760, a closure may be inserted into the head of the pedicle screw to secure the rod in place. The instrument includes a central cylindrical passage to allow the closure to be inserted without removing the rod reduction instrument 100, 200.

At 770, the rod reduction instrument may be removed from the head of the pedicle screw.

The instrument removal operation 770 can optionally include operations such as: selecting a mode at 772, rotating the instrument input at 774, activating the ratchet release button at 776, and disengaging the pedicle screw at 778. In certain examples, after selecting a mode 772 such as the Quick On/Off mode, the ratchet mechanism 120 in the Quick On/Off mode may not be able to release the tension on the rod reduction instrument 100. In such a scenario, the instrument can be shifted into the fixed mode through manipulation of the slide lock 132 into the proximal position. In the fixed mode, the top sleeve 215 can be rotated at 774 to release tension on the outer housing 110 from engagement with the connecting rod. Once the tension is released, the mode can be shifted back to the Quick On/Off mode, and the ratchet release button 142 can be activated at 776. Activating the ratchet release button 142 allows the outer housing 110 to slide in reference to the inner sleeve 101 to open the instrument. Once the instrument is open, the engagement members 103 can be disengaged from the pedicle screw head at 778.

FIGS. 8A-10D are various views illustrating a rapid rod reduction instrument 800 (e.g., a rocket reducer 800) with a ratchet mechanism 813, in accordance with example embodiments of the present disclosure. It is noted that embodiments of the rod reduction instrument 100 with the ratchet mechanism 120 illustrated in FIGS. 1A-3J and/or the rod reduction instruments 200 with the ratchet mechanism 220 illustrated in FIGS. 4-6J may be directed to the rod reduction instrument 800 with the ratchet mechanism 813 illustrated in FIGS. 8A-10D, and vice versa. In one non-limiting example, the various ratchet mechanisms without lock-out capabilities discussed above in reference to FIGS. 1A-6J can be integrated into the rod reduction instrument 800 discussed in reference to FIGS. 8A-10D. For instance, the ratchet mechanism 220 with slide lock 232 discussed in reference to FIGS. 6A-6J can be integrated into the ratchet mechanism 813 illustrated above in reference to the rod reduction instrument 800, without departing from the scope of the present disclosure.

Figure 8A:
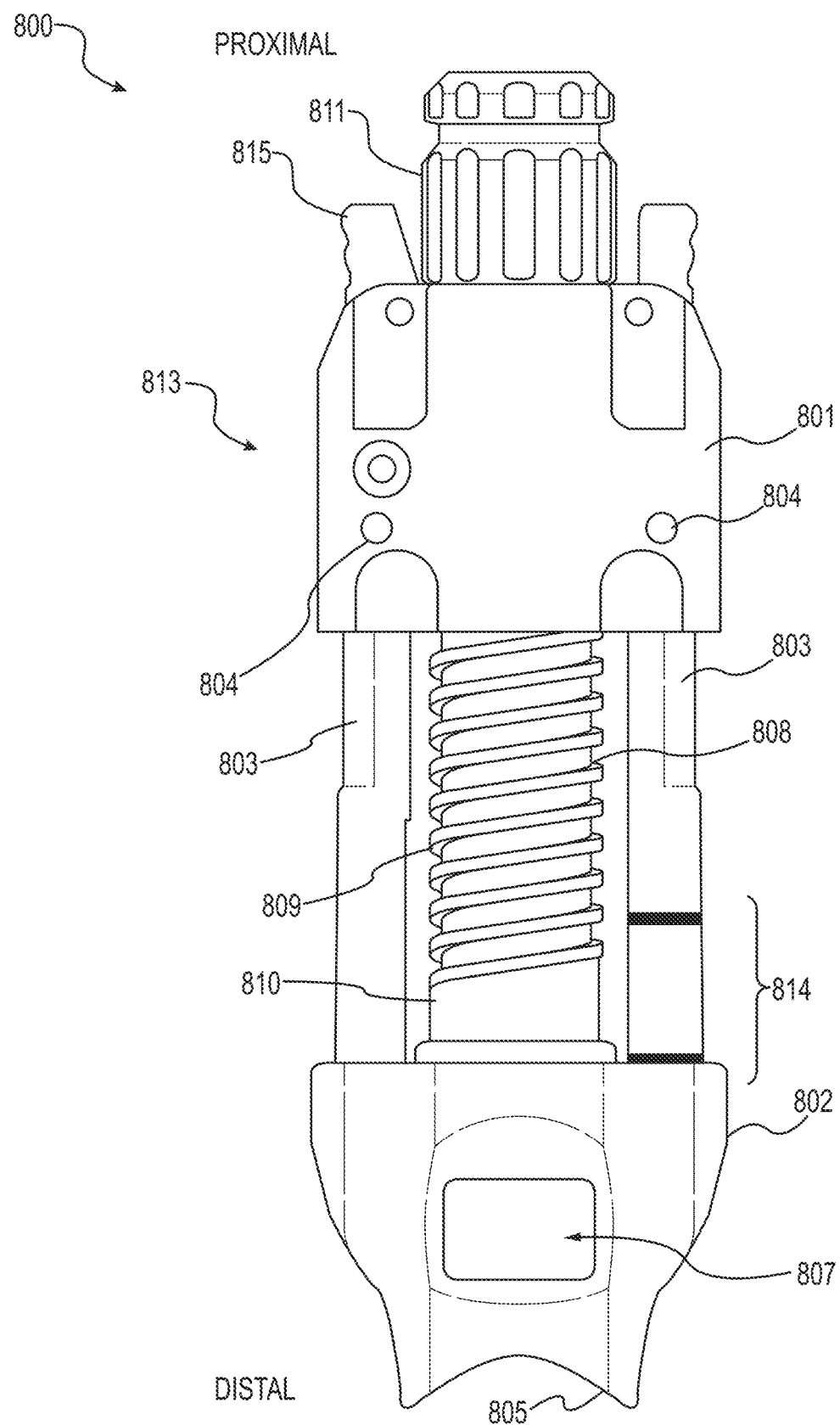
FIGS. 8A-8F are diagrams and drawings of a rod reduction instrument, in accordance with example embodiments of the present disclosure.
Figure 8B:
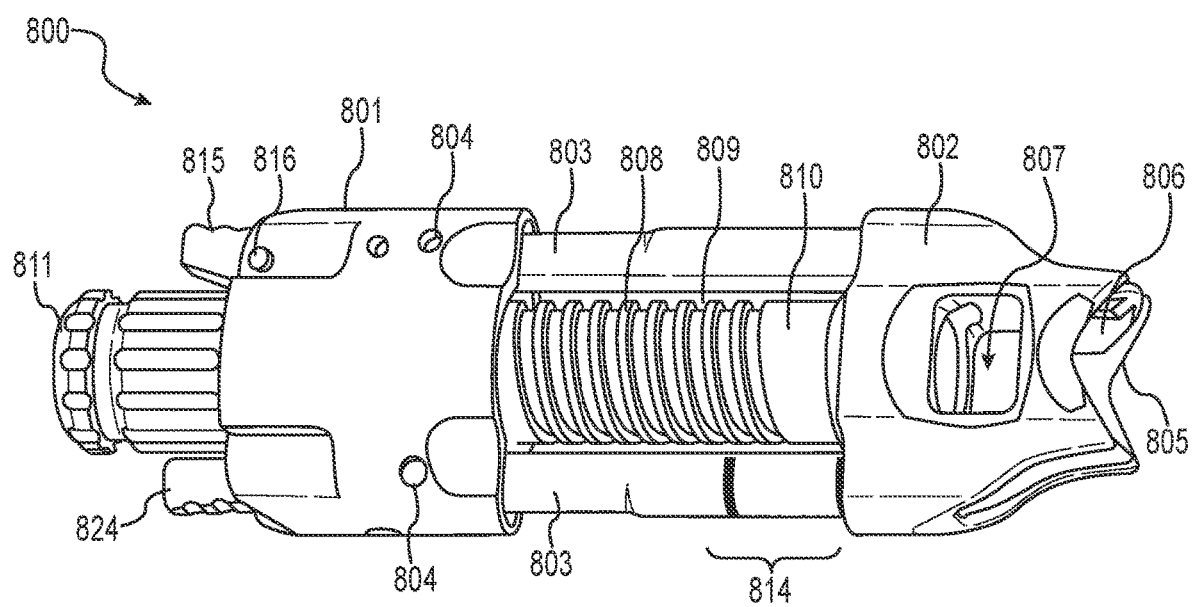
Figure 8C:
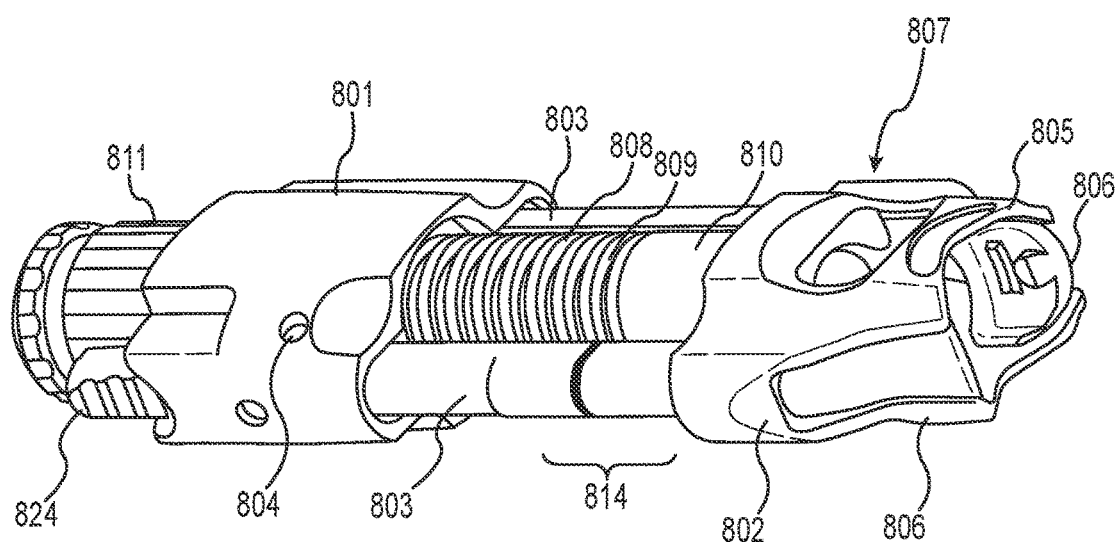
Figure 8D:
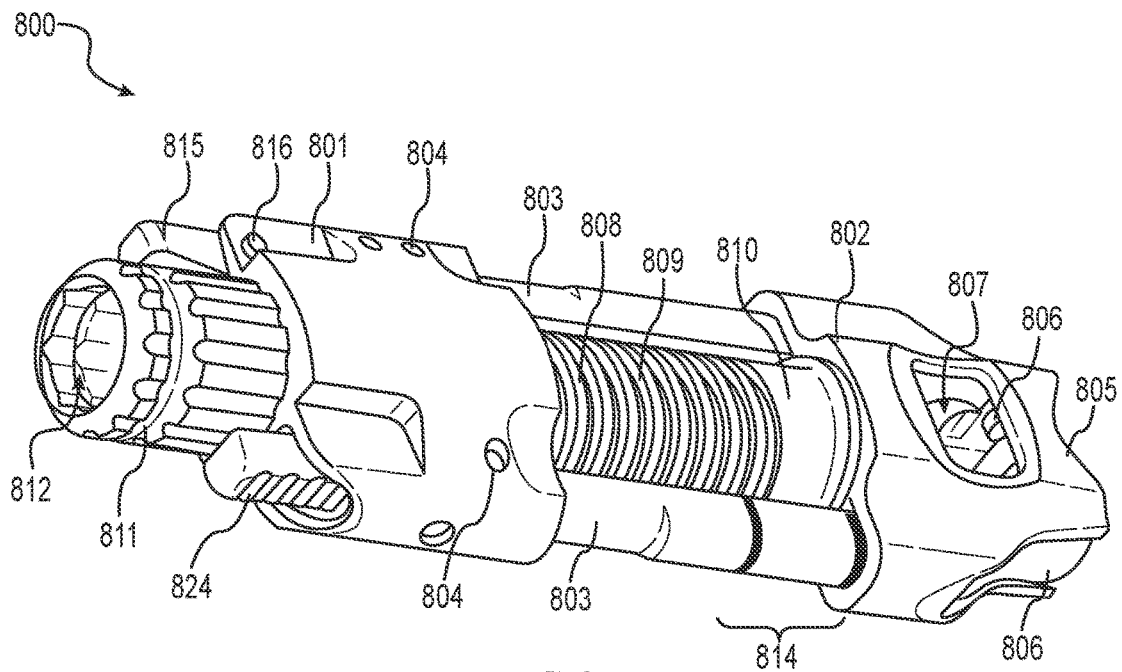
Figure 8E:
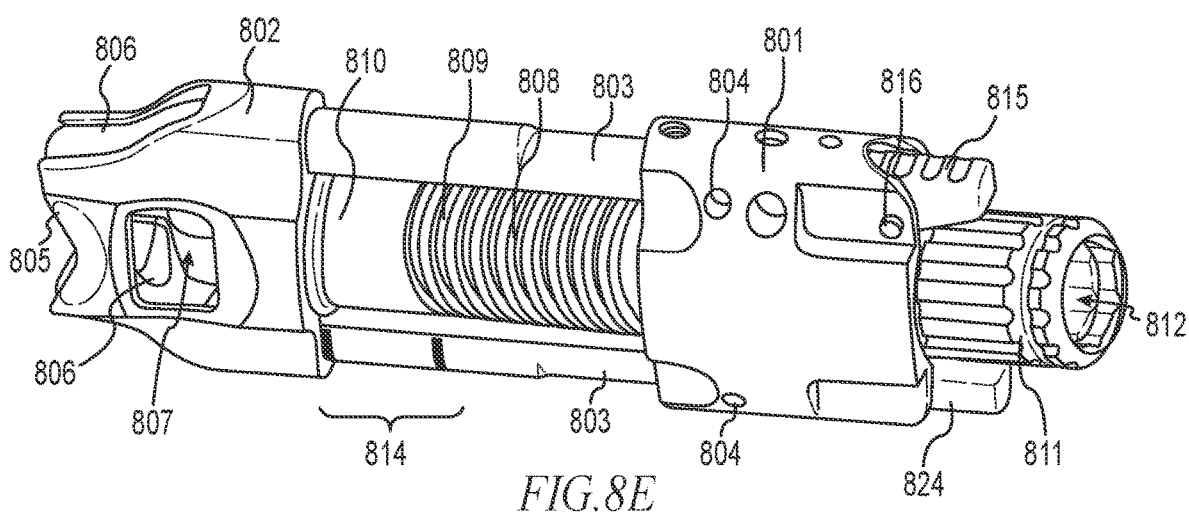
Figure 8F:
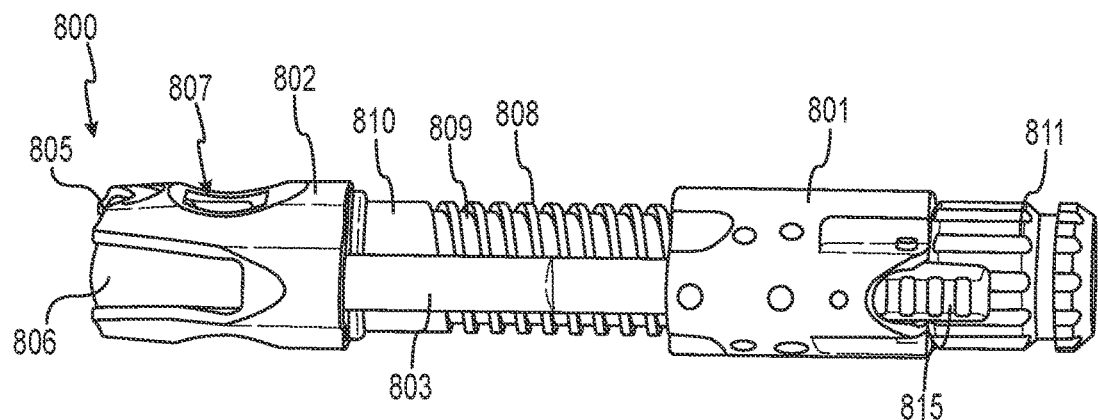

FIGS. 8A-8F include diagrams and drawings of the rod reduction instrument 800 with the ratchet mechanism 813, in accordance with example embodiments of the present disclosure. In particular, FIG. 8A is a solid model front view, FIG. 8B is a first perspective view, FIG. 8C is a second perspective view, FIG. 8D is a third perspective view, FIG. 8E is a fourth perspective view, and FIG. 8F is a fifth perspective view of the rod reduction instrument 800 with the ratchet mechanism 813.

The rod reduction instrument 800 can include an upper housing 801 (or first housing portion 801) and a lower housing 802 (or second housing portion 802). The upper housing 801 and the lower housing 802 can be coupled together via one or more components. The rod reduction instrument 800 can include one or more support members 803. The one or more support members 803 may be positioned within the upper housing 801 and affixed via a pin 804. For example, the pin 804 may be coupled to, or be a single integrated component formed with, a support member 803. For instance, the pin 804 may be inserted within the upper housing 801 and the support member 803. In addition, the pin 804 may be a protrusion formed on a surface of the support member 803 and configured to engage an aperture or recess defined within a sidewall of the upper housing 801. The one or more support members 803 may be capable of passing through the lower housing 802.

It is noted the lower housing 802 may be operable to receive a pedicle screw. For example, the lower housing 802 may include a rod engagement location 805. For example, the rod engagement 805 may include a cut-out (e.g., semicircular, or generally configured to conform to an edge or surface of a connecting rod) on opposing sides of a distal end of the lower housing 802. By way of another example, the rod engagement 805 may include a cavity dimensioned to accept a housing on a pedicle screw that receives the connecting rod.

The one or more support members 803 can include one or more engagement members 806 which are adapted to engage the housing on the pedicle screw. For example, the one or more engagement members 806 may be configured to receive an edge or surface of the housing to hold the pedicle screw and the rod reduction instrument 800 together and/or stabilize the rod reduction instrument 800 against the pedicle screw.

The lower housing 802 can include a window or aperture 807. For example, the window or aperture 807 can receive an interlocking component, where the interlocking components is configured to pass through the lower housing 802 and the pedicle screw to temporarily secure the rod reduction instrument 800 to the pedicle screw. By way of another example, the window or aperture 807 can receive other components that engage or operate with the pedicle screw (e.g., closures, alignment rods, connecting rods, or the like).

The rod reduction instrument 800 can include an inner sleeve 808. For example, the inner sleeve 808 may be at least partially positioned within a space defined between the upper housing 801 and the lower housing 802. Where there are multiple support members 803, the inner sleeve 808 may be positioned within a space defined between the multiple support members 803. For example, the multiple support members 803 may be diametrically opposed to one another, with the inner sleeve 808 positioned within the middle. In this example, the space through which the inner sleeve 808 may pass is defined by the upper housing 801, the lower housing 802, and the diametrically opposed support members 803. It is noted, however, the multiple support members 803 may be non-diametrically opposed and/or may be positioned proximate to one side of the inner sleeve 808, without departing from the scope of the present disclosure.

At least a portion of the inner sleeve 808 can include threading. For example, a first portion 809 of the inner sleeve 808 may include threading and at least a second portion 810 of the inner sleeve 808 may be non-threaded. By way of another example, the entire inner sleeve 808 may include threading. In one non-limiting example, the inner sleeve 808 may be considered a threaded reduction shaft.

The inner sleeve 808 can pass through the upper housing 801. A proximal end of the inner sleeve 808 may be coupled to, or be a single integrated component with, an actuator 811. Engaging the actuator 811 can cause the inner sleeve 808 to rotate within the space defined between the upper housing 801 and the lower housing 802. For example, the actuator 811 may be manually actuated or adjusted by a user via engagement of an external surface. By way of another example, the actuator 811 may be actuated by a user via a tool (e.g., a T-handle; a hex wrench, a screwdriver, or other tool with a common or proprietary bit; or the like). For instance, the actuator 811 may include a socket or other tool engagement surface 812 configured to receive the tool. By way of another example, the actuator 811 may be actuated by a user via a secondary device including, but not limited to, a robotic arm. It is noted a "tool engagement surface" and a "tool socket" may be considered equivalent, for purposes of the present disclosure.

It is contemplated the actuator 811 may be positioned proximate to an exterior top surface of the upper housing 801. Alternatively, the inner sleeve 808 may be coupled to, or be a single integrated component formed with, an upper sleeve and spaced a select distance from the exterior top surface of the upper housing 801. Where there is an upper sleeve, the actuator 811 may be coupled to, or be a single integrated component formed with, the upper sleeve.

The inner sleeve 808 can be configured to engage the lower housing 802. For example, engaging the lower housing 802 may prevent the inner sleeve 808 from passing through the lower housing 802 when the inner sleeve 808 is rotated by the actuator 811, while still allowing for the rotation of the inner sleeve 808. This engagement may allow for the upper housing 801 to be displaced relative to the lower housing 802 between a first state or configuration and a second, different state or configuration, with assistance from a ratchet mechanism 813. For example, the states or configuration may differ in at least a spacing or height between the upper housing 801 and the lower housing 802. In this example, the lower housing 802 may have a stopper which prevents the passing of the inner sleeve 808 through the lower housing 802. Alternatively, or in addition, a flange that engages a top surface of the lower housing 802 may be coupled to, or be a single integrated component formed with, the inner sleeve 808.

It is noted, however, the components of the rod reduction instrument 800 may be arranged to allow the inner sleeve 808 to be capable of passing through the lower housing 802, while still allowing for a displacement of the upper housing 801 and the support members 803 with engagement members 806 relative to the lower housing 802, without departing from the scope of the present disclosure.

The rod reduction instrument 800 may include one or more labels or markings 814 which indicate a displacement of the support members 803. For example, the labels or markings 814 may include, but are not limited to, lines, dots, or another graphical representation which are readable relative to an edge, surface, aperture, or the like of the lower housing 802. By way of another example, the labels or markings 814 may be printed on the support members 803, applied with a sticker to the support members 803, and/or integrated with the support members 803 (e.g., a recess or a protrusion). It is noted that engaging the actuator 811 and causing the inner sleeve 808 to rotate may displace the support members 803 with engagement members 806. For example, rotation in a first direction may displace the support members 803 downward, such that the engagement members begin or continue to exit from a bottom surface of the lower housing 802. Displacement of the support members 803 may cause a shift between a first state or configuration as indicated by a first label or marking 814 being read relative to the lower housing 802 and a second, different state or configuration indicated by a second, different label or marking 814 being read relative to the lower housing 802.

Figure 9A:
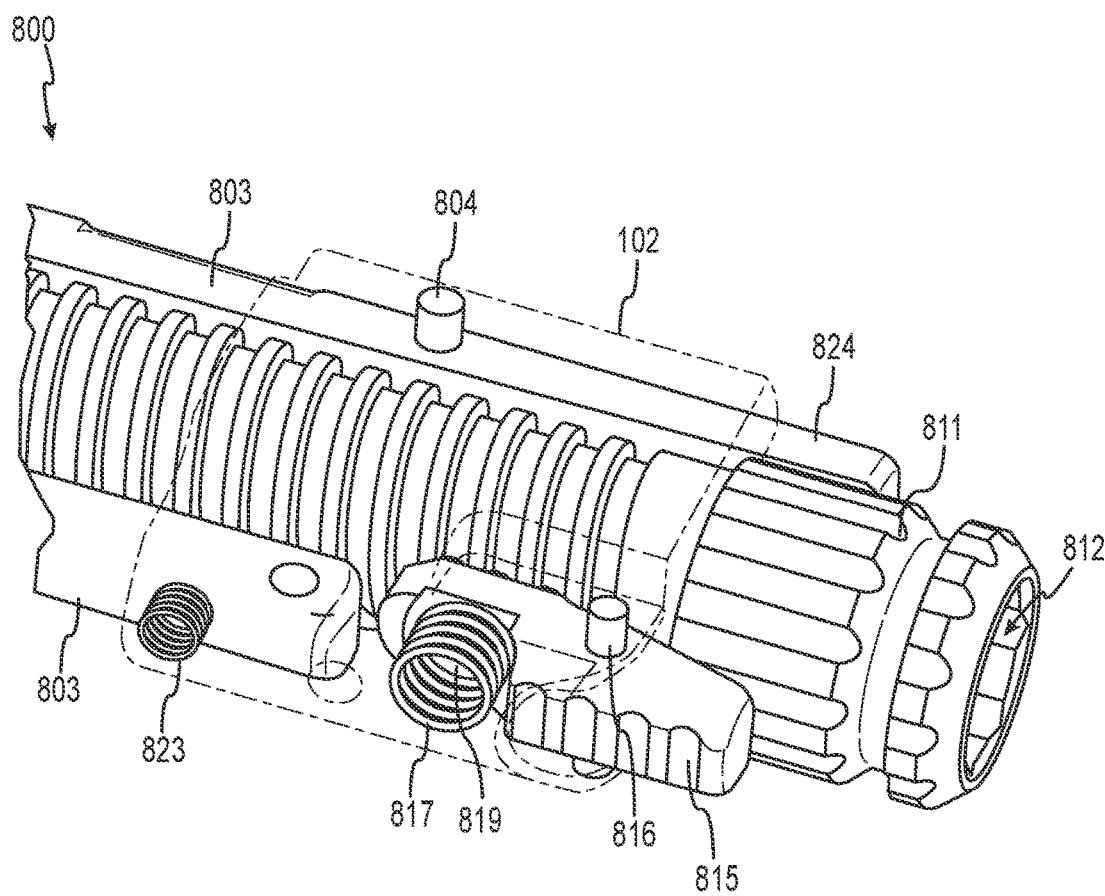
FIGS. 9A-9B are diagrams and drawings of a front view of a rod reduction instrument with a transparent upper housing, in accordance with example embodiments of the present disclosure.
Figure 9B:
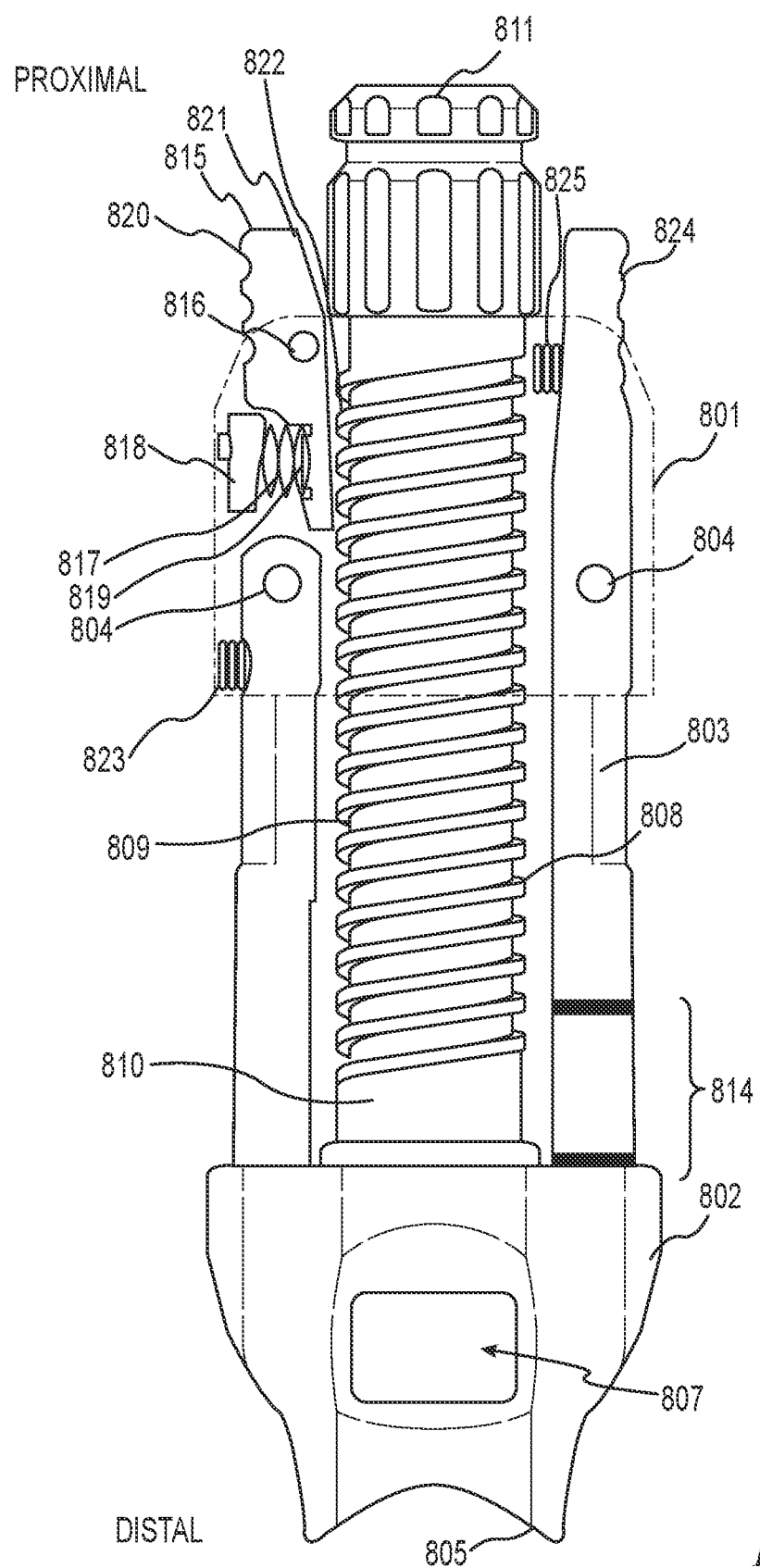
Figure 10A:
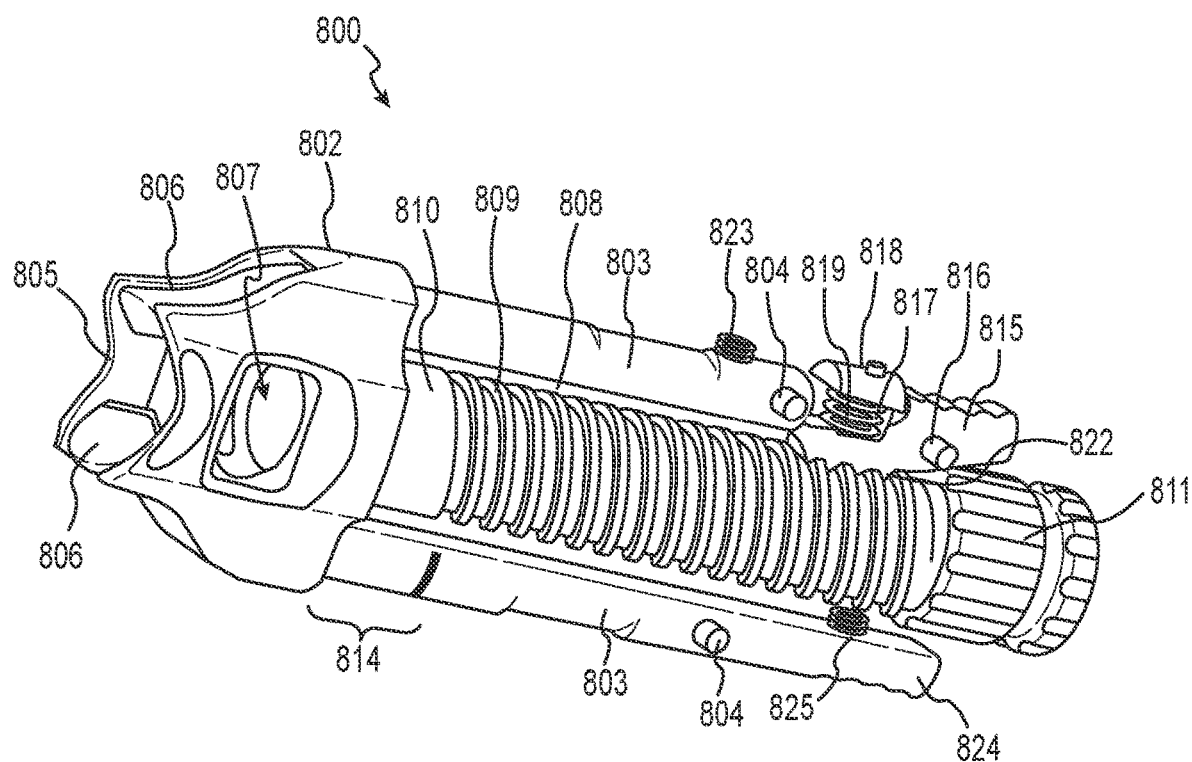
FIGS. 10A-10D are diagrams and drawings of a rod reduction instruments without an upper housing, in accordance with example embodiments of the present disclosure.
Figure 10B:
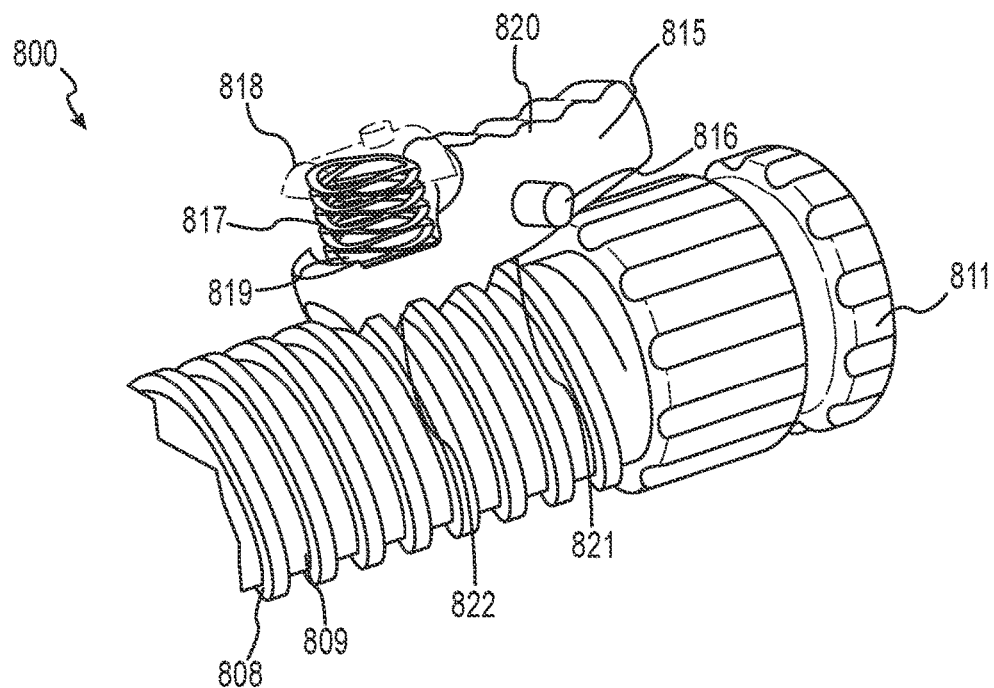
Figure 10C:
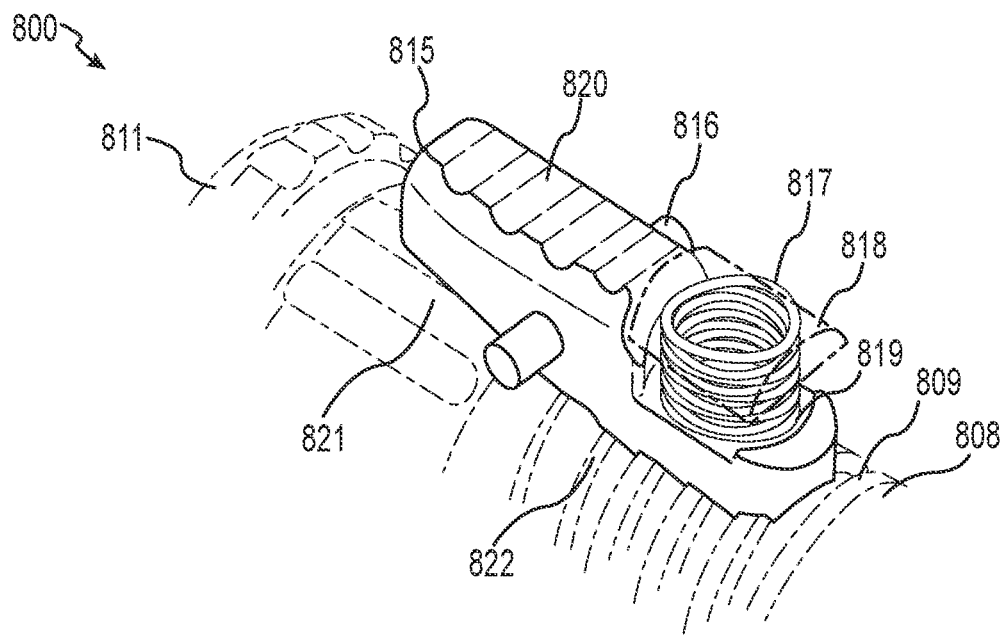
Figure 10D:
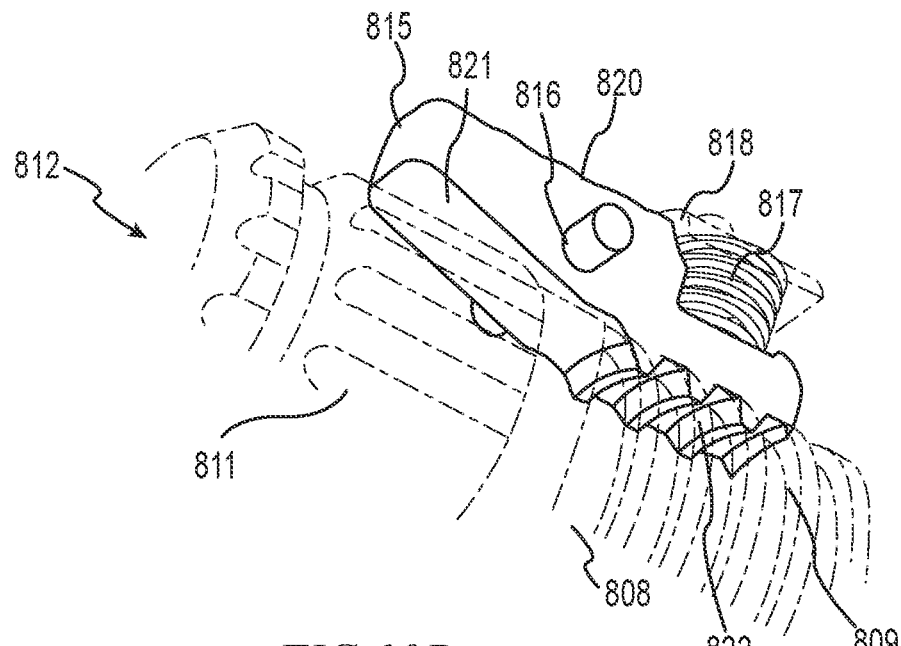

FIGS. 9A-10D include diagrams and drawings of the rod reduction instrument 800 with the ratchet mechanism 813, in accordance with example embodiments of the present disclosure. In particular, FIG. 9A illustrates a perspective view and FIG. 9B illustrates a solid model front view of the rod reduction instrument 800 with a transparent upper housing 801 for ease of clarity with respect to components of the ratchet mechanism 813. In addition, FIG. 10A illustrates a perspective view, FIG. 10B illustrates a partial perspective view, FIG. 10C illustrates a second partial perspective view, and FIG. 10D illustrates a third partial perspective view of the upper housing 801 having been removed from the rod reduction instrument 800 for ease of clarity with respect to components of the ratchet mechanism 813. Further, it is noted the inner sleeve 808 of the rod reduction instrument 800 is transparent in FIGS. 10C and 10D for increased ease of clarity with respect to select components of the ratchet mechanism 813.

The ratchet mechanism 813 may include a ratchet lever 815. The ratchet lever 815 may be at least partially positioned within the upper housing 801 and affixed via a pin 816. For example, the pin 816 may be coupled to, or be a single integrated component formed with, the ratchet lever 815. For instance, the pin 816 may be inserted within the upper housing 801 and the ratchet lever 815. In addition, the pin 816 may be a protrusion formed on a surface of the ratchet lever 815 and configured to engage an aperture or recess defined within a sidewall of the upper housing 801.

The ratchet mechanism 813 may include a bias spring 817 positioned between the upper housing 801 and the ratchet lever 815. For example, a shim 818 may be positioned within the upper housing 801 between the bias spring 817 and the upper housing 801, with which the bias spring makes contact. By way of another example, a surface 819 of the ratchet lever 815 may include a protrusion that fits within the bias spring 817 (or groove in which the bias spring 817 rests) and prevents the bias spring 817 from moving.

The ratchet lever 815 may include a first surface 820 and a second surface 821. For example, at least a portion of the second surface 821 may be diametrically opposite from the first surface 820. The second surface 821 may include threading or teeth 822 which is mated to the threading 809 on the inner sleeve 808. This mating allows the inner sleeve 808 to engage the upper housing 801 (and thus the support members 803) via the ratchet mechanism 813. For example, as the threading or teeth 822 is mated with the threading 809, rotating the inner sleeve 808 may cause the upper housing 801 and the support members 803 to be displaced between a first state or configuration and a second state or configuration. It is noted the threading or teeth 822 may be considered an engagement feature of the ratchet mechanism 813, for purposes of the present disclosure.

The ratchet mechanism 813 may provide the rod reduction instrument 800 with a quick on, quick off feature as described throughout the present disclosure (also referred to as Quick On/Off mode), where the threading or teeth 822 are configured to be disengaged from the threading 809. When the ratchet mechanism 813 is not engaged, the rod reduction instrument 800 is in a fixed mode as described throughout the present disclosure, where the threading or teeth 822 are configured to be engaged from the threading 809 to allow for fine-tuning of the engagement by the engagement members 806.

The ratchet mechanism 813 can be shifted into a fixed mode or a fine-tuning operation, and/or threaded mode of operation, locking out the ratchet mechanism. As discussed in detail below, locking out the ratchet mechanism 813 involves forcing an engagement feature of the ratchet mechanism 813 into fixed engagement with a threaded portion of the inner sleeve 808. In this fixed mode, the reducer operates as a threaded reduction instrument, with no rapid translation of the upper housing 801. Accordingly, in the fixed mode the upper housing 801 translates based solely on rotation input received through the tool engagement surface 812 (or any rotation of the actuator 811). Shifting the ratchet mechanism 813 of the rod reduction instrument 800 into the fixed mode enables a user to remove the reduction instrument from difficult reduction scenarios, where a ratcheting reduction instrument may not function properly due to high reduction forces. For example, because ratcheting instruments typically rely upon some form of biasing element, such as a coil spring, to keep a threaded member engaged with the threaded inner sleeve, in certain situations the coils spring can fail to keep the threads engaged sufficiently to overcome forces operating on the instrument. In these situations, a ratcheting only instrument may have to be removed through extraordinary measures, such as cutting the connecting rod and removing the pedicle screw. A dual mode ratchet mechanism 813 with a lock-out capability can avoid such extraordinary measures by providing a mechanism to fix engagement of the threading or teeth 822 of the ratchet mechanism 813 against the threading 809 of the inner sleeve 808. In the fixed engagement mode, the rod reduction instrument 800 can leverage the mechanical advantage of the threading 809, 822 to overcome external forces jamming the rod reduction instrument 800.

A user may apply an external force to the first surface 820 to cause the ratchet lever to pivot about the pin 816. It is noted the pin 816 may allow the ratchet lever 815 to pivot relative to the inner sleeve 808. Pivoting the ratchet lever 815 may cause the threading or teeth 822 to engage or disengage the threading 809 of the inner sleeve 808. This pivoting allows for the quick engaging or disengaging from the threading 809 instead of having to use the actuator 811, decreasing the necessary time for the rod reduction instrument 800 to be positioned relative to the pedicle screw. In addition, it is noted the bias spring 817 may be compressed when the ratchet lever 815 is pivoted to disengage the threading 809 via the external force applied by the user, which may return the ratchet lever 815 to an engaged position where it mates with the threading 809 when the external force is removed. In this regard, the bias spring 817 (and corresponding components 817, 819, etc.) may be considered a locking mechanism 813 of the rod reduction instrument 800, for purposes of the present disclosure.

It is noted the ratchet mechanism 813 may be considered to include at least some portion of one or more of the upper housing 801, the inner sleeve 808 with threading 809, and the support members 803 in addition or instead of the components listed in the above-described embodiments and examples without departing from the scope of the present disclosure.

The upper housing 801 may house one or more bias springs 823 for the one or more support members 803. The one or more bias springs 823 may provide a force which causes the one or more engagement members 806 of the support members 803 to engage the housing of the pedicle screw.

The rod reduction mechanism 813 includes a pedicle screw release lever 824. For example, the pedicle screw release lever 824 may be coupled to, or a single integrated component formed with, a support member 803. The pedicle screw release lever 824 may be positioned to prevent interference with, and/or accidental engaging or disengaging with, the ratchet lever 815. For example, the pedicle screw release lever 824 may be positioned diametrically opposite from the ratchet lever 815, to allow a user to engage one with their palm and the other with their fingers with the same hand.

The pedicle screw release lever 824 may be biased against the upper housing 801 by one or more bias springs 825. Where the pedicle screw release lever 824 is coupled to, or a single integrated component formed with, a support member 803, the bias springs 823 and the bias springs 823 may be the same spring or a different spring.

It is noted that any springs may be replaced with similar components including, but not limited to, a biased living hinge or other structure pre-loaded with a return force which may be overcome through application of an external force (e.g., by a user), without departing from the scope of the present disclosure.

In one non-limiting example, the ratchet lever 815 and the pedicle screw release lever 824 may be distinguishable to provide visual and/or haptic aid to assist in operation of the device. For example, the ratchet lever 815 and the pedicle screw release lever 824 may be formed or painted with a different color (e.g., including, but not limited to, a yellow or gold color), may be fabricated from a different material, may include a different pattern or design on the grip and/or for the entire body, and/or may include other distinguishing features or characteristics. In one non-limiting example, the rod reduction instrument 800 has two diametrically opposed support members 803. The ratchet lever 815 may be positioned within the upper housing 801 above a first of the support members 803, while a second support member 803 includes the pedicle release lever 824. In this regard, the first support member 803 may be shorter in length than the second support member 803. However, both support members 803 include engagement members 806 positioned at the same relative location within the lower housing 802.

Figure 11:
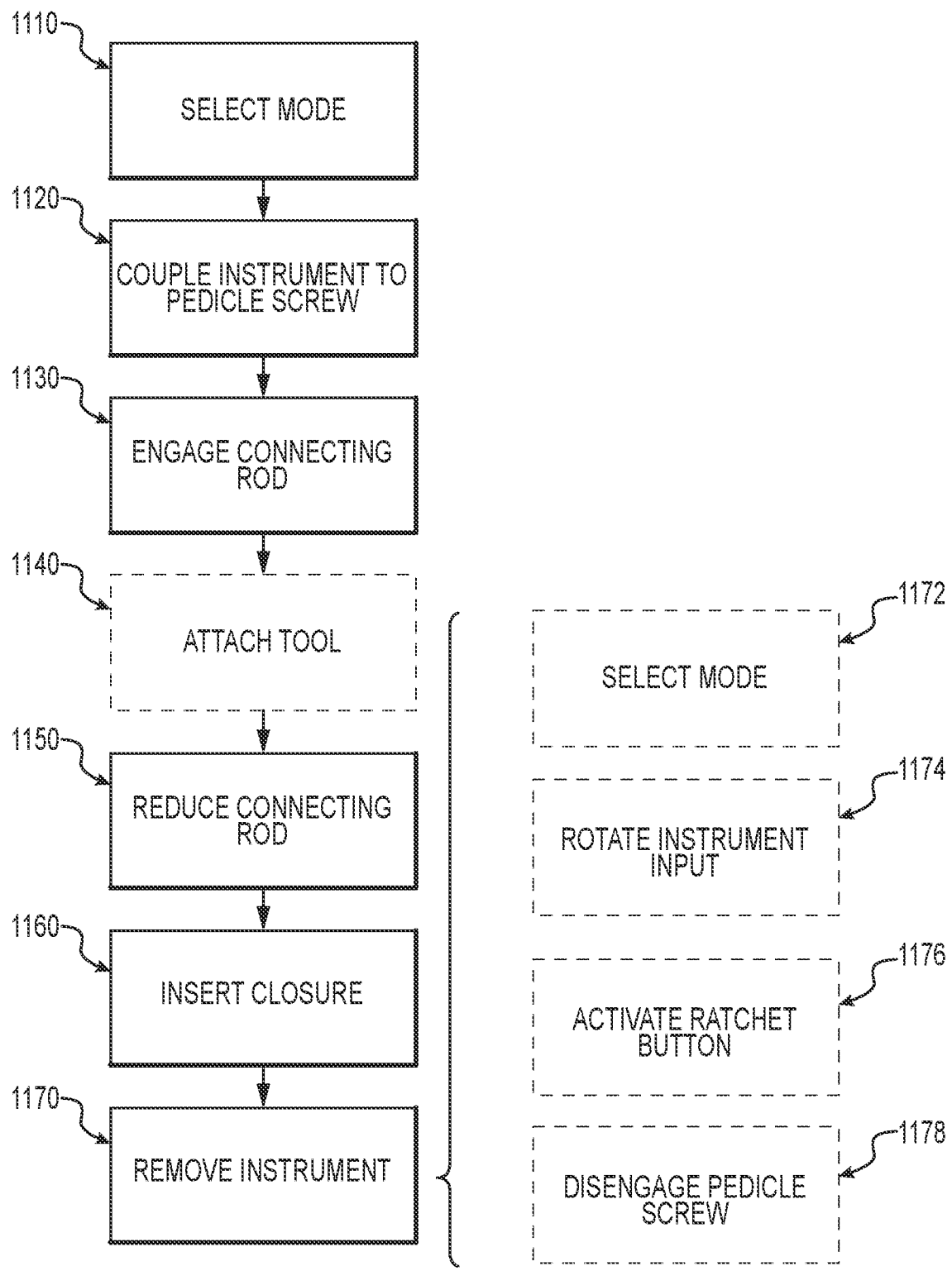
FIG. 11 is a flowchart illustrating a method for using a rod reduction instrument, in accordance with example embodiments of the present disclosure.

FIG. 11 is a flowchart illustrating a method 1100 for using a rod reduction instrument 800. In this regard, the steps or processes 1100 may cause an adjustment of and/or be performed by the components of the rod reduction instrument 800.

The method 1100 illustrates a common set of operations utilizing one of the rod reduction instruments discussed above. However, the method 1100 does not cover all possible uses of the instruments, the operations discussed can be done in a different sequence, operations could be repeated or omitted, as fits the particular scenario of use. In this example, the method 1100 can include operations such as: selecting a Quick On/Off mode or fixed mode at 1110, coupling to a pedicle screw at 1120, engaging a connecting rod at 1130, optionally attaching a tool at 1140, reducing the connecting rod at 1150, inserting a closure into the pedicle screw at 1160, and removing the rod reduction instrument at 1170. The operations discussed in method 1100 are depicted in a common order of operation, but many of the operations can be shifted into other positions in the method or repeated. For example, the mode of operation can be switched at any point during the procedure.

At 1110, the mode of operation of the instrument may be selected. In this example, a user may elect to engage the ratchet lever 815 or utilize the actuator 811. With the ratchet lever 815 engaged (e.g., in a Quick On/Off mode0, the ratchet mechanism is free to ratchet, as the threading or teeth 822 of the ratchet lever 815 are not mated with the threading 809 of the inner sleeve 808. This allows for a fast reduction of distance to the pedicle screw. In another example, the user may choose to engage the threaded operation mode by only engaging the actuator 811 (e.g., in a fixed mode). This allows for a fine-tuning of positioning with respect to the pedicle screw.

At 1120, the rod reduction instrument 800 may be coupled to a head of a pedicle screw. For example, engagement members 806 of the rod reduction instrument 800 may be placed into engagement with the head of a pedicle screw. Prior to engaging the pedicle screw, the inner sleeve 808 may be fully extended into a fully open position. In an example, the instrument may include four separate engagement members that engage four vertical slots on the screw head. In other examples, the instrument may only include two engagement members that engage either arm of a pedicle screw head.

At 1130, a connecting rod may be engaged once the head of the pedicle screw is engaged. In this example, where the ratchet lever 815 were engaged, being in the Quick On/Off mode, the connecting rod may be quickly engaged through ratcheting. If the ratchet lever 815 were not engaged via an application of an external force, being in the fixed mode, an external force applied (e.g., such as a rotational input) to the actuator 811 would be necessary to engage the connecting rod.

Optionally at 1140, a tool may be attached to the actuator 811 via the tool engagement surface (or tool socket) 812. For example, the tool may include, but is not limited to, a T-handle; a hex wrench, a screwdriver, or other tool with a common or proprietary bit; or the like. It is noted the tool engagement surface 812 may be manually actuated or adjusted, however, without departing from the scope of the present disclosure.

At 1150, the rod reduction instrument 800 may be manipulated to reduce the connecting rod into the head of the pedicle screw. Instrument manipulation may include rotation of the tool (or manual actuation of the actuator 811 if no extra torque is needed), which causes translation of the upper housing 801.

At 1160, a closure may be inserted into the head of the pedicle screw to secure the rod in place. The window or aperture 807 may configured to receive and allow a closure to be inserted without removing the rod reduction instrument 800.

At 1170, the rod reduction instrument 800 may be removed from the head of the pedicle screw.

The instrument removal operation 1170 can optionally include operations such as: selecting a mode at 1172, rotating the instrument input at 1174, activating the ratchet release button at 1176, and disengaging the pedicle screw at 778. At 1172, a mode is again selected. For example, the user may elect to apply an external force to the ratchet lever 815 or to the actuator 811. For instance, where the force is applied to the actuator 811, instrument manipulation may include rotation of the tool (or manual rotation of the actuator 811 if no extra torque is needed) at 1174, which causes translation of the upper housing 801. In addition, where the force is applied to the ratchet lever 815 at 1176, the threading or teeth 822 are un-mated from the threading 809 of the inner sleeve 808, allowing for quick or rapid ratcheting. At 1178, the rod reduction instrument 800 may disengage from the pedicle screw. It is noted that applying the external force to the ratchet lever 815 may afford a much quicker disengaging from the pedicle screw than if the external force were allowed to the actuator 811.

Each of the following non-limiting examples may stand on its own, or may be combined in various permutations or combinations with one or more of the other examples.

Example 1 describes subject matter that can include a rod reduction instrument. In this example, the rod reduction instrument can include an inner sleeve, an outer housing, and a ratchet mechanism. The inner sleeve can include a threaded proximal portion and a distal end, the distal end including a plurality of engagement members adapted to receive a housing of a pedicle screw. The outer housing can be slidably received over at least a portion of the inner sleeve. The outer housing can also include a top sleeve and a bottom sleeve. In this example, the distal end of the bottom sleeve is adapted to engage a connecting rod. The ratchet mechanism can be disposed along the top sleeve of the outer housing. In this example, the ratchet mechanism can include an engagement feature to selectively engage the threaded proximal portion of the inner sleeve, and a locking mechanism to selectively lock the engagement feature of the ratchet mechanism against the threaded proximal portion of the inner sleeve.

In Example 2, the subject matter of Example 1 can optionally include the top sleeve being rotatably coupled to the bottom sleeve and adapted to convert rotational input into linear translation of the outer housing relative to the inner sleeve.

In Example 3, the subject matter of Example 2 can optionally include the engagement feature of the ratchet mechanism engaging the threaded proximal portion of the inner sleeve, upon receiving rotational input from the top sleeve, to linearly translate the outer housing along a longitudinal axis in relation to the inner sleeve.

In Example 4, the subject matter of any one of Examples 1 to 3 can optionally include the ratchet mechanism having a lever member including a proximal end and a distal end separated by a pivot.

In Example 5, the subject matter of Example 4 can optionally include the engagement feature of the proximal end of the lever member being adapted to selectively engage the threaded proximal portion of the inner sleeve.

In Example 6, the subject matter of any one of Examples 4 and 5 can optionally include the distal end of the lever member having a button exposed on an external surface of the ratchet mechanism.

In Example 7, the subject matter of any one of Examples 4 to 6 can optionally include the pivot having a pivot pin extending into opposing side walls of the locking mechanism, which enables rotational movement of the lever member about the pivot pin.

In Example 8, the subject matter of Example 7 can optionally include the engagement feature on a proximal portion of the lever member selectively engaging the threaded proximal portion of the inner sleeve through the rotational movement of the lever member.

In Example 9, the subject matter of Example 8 can optionally include the ratchet mechanism having a biasing member positioned against a superior surface of the proximal portion of the lever member opposite the engagement feature to bias the engagement feature against the threaded proximal portion of the inner sleeve.

In Example 10, the subject matter of any one of Examples 4 to 9 can optionally include the locking mechanism having a slide lock disposed on an external surface of the ratchet mechanism adapted to lock the locking mechanism in a first position and unlock the locking mechanism in a second position.

In example 11, the subject matter of Example 10 can optionally include the slide lock being a linear slide slidably engage along opposing sides of the ratchet mechanism, the slide lock translates along a longitudinal axis of the rod reduction instrument between the first position and the second position.

In Example 12, the subject matter of Example 11 can optionally include the slide lock including a transverse pin projecting from an inferior surface of the slide lock towards the longitudinal axis to engage a locking surface on the lever member.

In Example 13, the subject matter of Example 12 can optionally include the slide lock being in the first position so the transverse pin engages the locking surface to prevent the lever member from pivoting the engagement feature of the lever member away from the threaded proximal portion of the inner sleeve.

In Example 14, the subject matter of Example 12 can optionally include the slide lock being in the second position so the transverse pin is positioned over a cavity in the lever member allowing the lever member to pivot freely within the ratchet mechanism.

In Example 15, the subject matter of Example 10 can optionally include the slide lock being a stepped cylindrical shaft positioned transverse the lever member and disposed within a bore extending across a portion of a width of the ratchet mechanism.

In Example 16, the subject matter of Example 15 can optionally include the stepped cylindrical shaft including a large diameter section coupled to a small diameter section, the large diameter section engageable with a locking surface on the lever member to prevent pivoting of the lever member within the ratchet mechanism.

In Example 17, the subject matter of any one of Examples 15 or 16 can optionally include the slide lock translating within the bore between the first position and the second position.

In Example 18, the subject matter of Example 17 can optionally include the slide lock being in the first position where a portion of a larger diameter section of the stepped cylindrical shaft engages a locking surface on the lever member to lock-out the ratchet mechanism.

In Example 19, the subject matter of any one of Examples 15 to 18 can optionally include the locking mechanism including a biasing element disposed within the bore to bias the stepped cylindrical shaft into a particular position, such as the second position.

In Example 20, the subject matter of any one of Examples 15 to 19 can optionally include the stepped cylindrical shaft being biased into a second position where the lever member within the ratchet mechanism is free to pivot the engagement feature away from the threaded proximal portion of the inner sleeve allowing the outer housing to translate distally over the inner sleeve towards the pedicle screw without rotational input.

Example 21 describes subject matter that can include a rod reduction instrument. In this example, the rod reduction instrument can include an inner sleeve, a first housing portion, a second housing portion, a plurality of engagement members, and a ratchet mechanism. The inner sleeve can include a threaded proximal portion and a distal end. The first housing portion can be positioned over at least a portion of the inner sleeve. The second housing portion can be positioned proximate to the distal end of the inner sleeve. The plurality of engagement members can be adapted to receive a housing of a pedicle screw. In this example, the plurality of engagement members is positionable within the second housing portion. The ratchet mechanism can be at least partially disposed within the first housing portion. In this example, the ratchet mechanism can include an engagement feature to selectively engage the threaded proximal portion of the inner sleeve, and a locking mechanism to selectively lock the engagement feature of the ratchet mechanism against the threaded proximal portion of the inner sleeve.

Example 22 describes subject matter that can include a rod reduction instrument. In this example, the rod reduction instrument can include an inner sleeve, an upper housing, a lower housing, at least one support member, and a ratchet mechanism. The inner sleeve can include a threaded proximal portion and a distal end. The upper housing can be positioned over at least a portion of the inner sleeve. The lower housing can be positioned proximate to the distal end of the inner sleeve. The at least one support member can be coupled to the upper housing. In this example, a distal end of the at least one support member can include an engagement member positionable within the lower housing, where the engagement member is adapted to receive a housing of a pedicle screw. The ratchet mechanism can be at least partially disposed within the upper housing. In this example, the ratchet mechanism can include an engagement feature to selectively engage the threaded proximal portion of the inner sleeve, and a locking mechanism to selectively lock the engagement feature of the ratchet mechanism against the threaded proximal portion of the inner sleeve.

In Example 23, the subject matter of any one of Examples 1 to 22 can optionally include the engagement feature being selected from a group of structures including: threads, numbs, cylindrical protrusions, square or rectangular protrusions, and one or more detents with captured ball bearings.

In additional Examples, any one or more of the above aspects/embodiments as substantially disclosed herein.

In additional Examples, any one or more of the aspects/embodiments as substantially disclosed herein optionally in combination with any one or more other aspects/embodiments as substantially disclosed herein.

In additional Examples, one or means adapted to perform any one or more of the above aspects/embodiments as substantially disclosed herein.

In additional Examples, any one or more of the features disclosed herein.

In additional Examples, any one or more of the features as substantially disclosed herein.

In additional Examples, any one or more of the features as substantially disclosed herein in combination with any one or more other features as substantially disclosed herein.

In additional Examples, any one of the aspects/features/embodiments in combination with any one or more other aspects/features/embodiments.

In additional Examples, use of any one or more of the aspects or features as disclosed herein.

It is to be appreciated that any feature described herein can be claimed in combination with any other feature(s) as described herein, regardless of whether the features come from the same described embodiment.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. The transitional phrase "consisting of" excludes any element, step, or ingredient not specified in the claim, but does not exclude additional components or steps that are unrelated to the disclosure such as impurities ordinarily associated therewith. The transitional phrase "consisting essentially of" limits the scope of a claim to the specified materials or steps and those that do not materially affect the basic and novel characteristic(s) of the claimed invention. Moreover, in the following claims, the terms "first," "second," and "third," etc. are used merely as labels, and are not intended to impose numerical requirements on their objects.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The above description is intended to be illustrative, and not restrictive. For example, the above-described examples (or one or more aspects thereof) may be used in combination with each other. Other embodiments can be used, such as by one of ordinary skill in the art upon reviewing the above description. A number of variations and modifications of the disclosure can be used. It would be possible to provide for some features of the disclosure without providing others. In addition, it would be possible to combine some features of the disclosure without combining all.

References in the specification to "being operable" or "is operable" may be understood as "being configured to" or "is configured to," "being capable of" or "is capable of," and the like.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine," "calculate," "compute," and variations thereof, as used herein, are used interchangeably, and include any type of methodology, process, mathematical operation, or technique.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

Unless otherwise indicated, all numbers expressing quantities, dimensions, conditions, ratios, ranges, and so forth used in the specification and claims are to be understood as being modified in all instances by the term "about" or "approximately." Accordingly, unless otherwise indicated, all numbers expressing quantities, dimensions, conditions, ratios, ranges, and so forth used in the specification and claims may be increased or decreased by approximately 5% to achieve satisfactory results. Additionally, where the meaning of the terms "about" or "approximately" as used herein would not otherwise be apparent to one of ordinary skill in the art, the terms "about" and "approximately" should be interpreted as meaning within plus or minus 5% of the stated value.

All ranges described herein may be reduced to any sub-range or portion of the range, or to any value within the range without deviating from the invention. For example, the range "5 to 55" includes, but is not limited to, the sub-ranges "5 to 20" as well as "17 to 54."

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A rod reduction instrument comprising:
   an inner sleeve including a threaded proximal portion and a distal end;
   a plurality of support members, a distal end of each support member of the plurality of support members including an engagement member adapted to receive a housing of a pedicle screw;
   an outer housing slidably received over at least a portion of the inner sleeve, the outer housing including a top sleeve proximate to a proximal end of the rod reduction instrument and a bottom sleeve proximate to a distal end of the rod reduction instrument; and
   a ratchet mechanism at least partially disposed within the top sleeve of the outer housing, the ratchet mechanism including a lever member that extends in a direction toward the proximal end of the rod reduction instrument through an aperture of the top sleeve of the outer housing, the ratchet mechanism including an engagement feature to selectively engage the threaded proximal portion of the inner sleeve, the ratchet mechanism further including a locking mechanism to selectively lock the engagement feature of the ratchet mechanism when the engagement feature is engaged with the threaded proximal portion of the inner sleeve.

2. The rod reduction instrument of claim 1, wherein the top sleeve is rotatably coupled to the inner sleeve, wherein the top sleeve is adapted to convert rotational input of the inner sleeve into linear translation of the top sleeve relative to the inner sleeve, wherein upon receiving rotational input from the inner sleeve via engagement with the threaded proximal portion of the inner sleeve, the engagement feature of the ratchet mechanism causes the top sleeve to linearly translate along a longitudinal axis in relation to the inner sleeve.

3. The rod reduction instrument of claim 1, wherein the lever member includes a proximal end and a distal end separated by a pivot.

4. The rod reduction instrument of claim 3, wherein the distal end of the lever member includes the engagement feature adapted to selectively engage the threaded proximal portion of the inner sleeve.

5. The rod reduction instrument of claim 3, wherein the proximal end of the lever member includes an external surface of the ratchet mechanism that is operable to be engaged with by a user to cause the engagement feature to selectively engage the threaded proximal portion of the inner sleeve.

6. The rod reduction instrument of claim 3, wherein the pivot includes a pivot pin extending into opposing side walls of the top sleeve, and the pivot enables rotational movement of the lever member about the pivot pin.

7. The rod reduction instrument of claim 6, wherein the rotational movement of the lever member enables the engagement feature on a distal end of the lever member to selectively engage the threaded proximal portion of the inner sleeve.

8. The rod reduction instrument of claim 7, wherein the locking mechanism includes a biasing member positioned against a superior surface of the distal end of the lever member opposite the engagement feature to bias the engagement feature against the threaded proximal portion of the inner sleeve.

9. The rod reduction instrument of claim 1, wherein at least one support member of the plurality of support members is at least partially positioned within the top sleeve distal to and substantially longitudinally aligned with the lever member of the ratchet mechanism.

10. The rod reduction instrument of claim 9, wherein a proximal end of the at least one support member includes a pivot.

11. The rod reduction instrument of claim 10, wherein the pivot includes a pivot pin extending into opposing side walls of the top sleeve, and the pivot enables rotational movement of the at least one support member about the pivot pin.

12. The rod reduction instrument of claim 11, wherein the rotational movement of the at least one support member enables the engagement member of the at least one support member to receive the housing of the pedicle screw.

13. The rod reduction instrument of claim 12, further comprising a biasing member positioned against a superior surface of the proximal end of the at least one support member, wherein the biasing member enables the engagement member of the at least one support member to engage the housing of the pedicle screw.

14. The rod reduction instrument of claim 1, wherein at least one support member of the plurality of support members is at least partially positioned within the top sleeve on an opposing side of the inner sleeve relative to the lever member of the ratchet mechanism.

15. The rod reduction instrument of claim 14, wherein the at least one support member includes a pivot that separates a distal end and a proximal end of the at least one support member.

16. The rod reduction instrument of claim 15, further comprising a biasing member positioned against an inferior surface of the proximal end of the at least one support member, wherein the biasing member enables the engagement member of the at least one support member to engage the housing of the pedicle screw.

17. The rod reduction instrument of claim 15, wherein the proximal end of the at least one support member includes an external surface operable to be engaged with by a user to cause the engagement member to selectively disengage the housing of the pedicle screw.

18. The rod reduction instrument of claim 1, wherein at least one support member of the plurality of support members includes one or more markings configured to indicate a displacement of the support member relative to the bottom sleeve.

19. A rod reduction instrument comprising:
   an inner sleeve including a threaded proximal portion and a distal end;
   a first housing portion positioned over at least a portion of the inner sleeve;

a separate second housing portion positioned proximate to the distal end of the inner sleeve;

a plurality of engagement members adapted to receive a housing of a pedicle screw, the plurality of engagement members being positionable within the second housing portion; and a ratchet mechanism at least partially disposed within the first housing portion, the ratchet mechanism including a lever member that extends outward from a proximal end of the first housing portion toward a proximal end of the rod reduction instrument, the ratchet mechanism including an engagement feature to selectively engage the threaded proximal portion of the inner sleeve, the ratchet mechanism further including a locking mechanism to selectively lock the engagement feature of the ratchet mechanism when the engagement feature is engaged with the threaded proximal portion of the inner sleeve.

20. A rod reduction instrument comprising:

an inner sleeve including a threaded proximal portion and a distal end;

an upper housing positioned over at least a portion of the inner sleeve;

a lower housing positioned proximate to the distal end of the inner sleeve, wherein the lower housing and the upper housing are non-overlapping and separated by a gap between the upper housing and the lower housing along a longitudinal axis defined from a proximal end to a distal end of the rod reduction instrument;

at least one support member coupled to the upper housing, a distal end of the at least one support member including an engagement member positionable within the lower housing, the engagement member adapted to receive a housing of a pedicle screw; and a ratchet mechanism at least partially disposed within the upper housing, the ratchet mechanism including a lever member that extends toward a proximal end of the rod reduction instrument through an aperture of the upper housing, the ratchet mechanism including an engagement feature to selectively engage the threaded proximal portion of the inner sleeve, the ratchet mechanism further including a locking mechanism to selectively lock the engagement feature of the ratchet mechanism when the engagement feature is engaged with the threaded proximal portion of the inner sleeve.

\* \* \* \* \*